United States Patent
Berlin

(10) Patent No.: US 9,833,357 B2
(45) Date of Patent: *Dec. 5, 2017

(54) DELIVERY SYSTEM AND METHOD OF USE FOR THE EYE

(71) Applicant: Michael S. Berlin, West Hollywood, CA (US)

(72) Inventor: Michael S. Berlin, West Hollywood, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/288,993

(22) Filed: Oct. 7, 2016

(65) Prior Publication Data

US 2017/0020732 A1 Jan. 26, 2017

Related U.S. Application Data

(60) Continuation of application No. 14/028,460, filed on Sep. 16, 2013, now Pat. No. 9,603,741, which is a
(Continued)

(51) Int. Cl.
*A61M 5/00* (2006.01)
*A61F 9/007* (2006.01)
*A61F 9/008* (2006.01)

(52) U.S. Cl.
CPC ...... *A61F 9/00781* (2013.01); *A61F 9/00736* (2013.01); *A61F 9/00802* (2013.01);
(Continued)

(58) Field of Classification Search
CPC .............. A61F 9/00781; A61F 9/0017; A61F 9/00736; A61F 9/00802; A61F 2009/00868; A61F 2009/00891
(Continued)

(56) References Cited

U.S. PATENT DOCUMENTS 3,858,577 A 1/1975 Bass et al.
3,884,236 A 5/1975 Krasnov
(Continued)

FOREIGN PATENT DOCUMENTS

DE 19840047 A1 3/2000
EP 0898947 A2 3/1999
(Continued)

OTHER PUBLICATIONS

Berlin, et al. Excimer laser photoablation in glaucoma filtering surgery. American journal of ophthalmology 103.5 (1987): 713.
(Continued)

*Primary Examiner* — Philip R Wiest
(74) *Attorney, Agent, or Firm* — Wilson Sonsini Goodrich & Rosati

(57) ABSTRACT

A method and delivery system are disclosed for creating an aqueous flow pathway in the trabecular meshwork, juxtacanalicular trabecular meshwork and Schlemm's canal of an eye for reducing elevated intraocular pressure. Pulsed laser radiation is delivered from the distal end of a fiber-optic probe sufficient to cause photoablation of selected portions of the trabecular meshwork, the juxtacanalicular trabecular meshwork and an inner wall of Schlemm's canal in the target site. The fiber-optic probe may be advanced so as to create an aperture in the inner wall of Schlemm's canal in which fluid from the anterior chamber of the eye flows. The method and delivery system may further be used on any tissue types in the body.

24 Claims, 20 Drawing Sheets

Related U.S. Application Data continuation of application No. 11/970,488, filed on Jan. 7, 2008, now Pat. No. 8,540,659, which is a division of application No. 09/860,842, filed on May 21, 2001.

(60) Provisional application No. 60/205,846, filed on May 19, 2000.

(52) U.S. Cl.
CPC ............... *A61F 2009/00868* (2013.01); *A61F 2009/00891* (2013.01)

(58) Field of Classification Search
USPC .................. 604/27, 294, 246, 286, 523; 606/107–109, 151, 167; 600/398; 623/1.1, 4.1, 11.1, 1.35
See application file for complete search history.

(56) References Cited

U.S. PATENT DOCUMENTS

| | | |
|---|---|---|
| 3,982,541 A | 9/1976 | L'Esperance, Jr. |
| 4,273,109 A | 6/1981 | Enderby |
| 4,391,275 A | 7/1983 | Fankhauser et al. |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance, Jr. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,633,866 A | 1/1987 | Peyman et al. |
| 4,658,816 A | 4/1987 | Ector, Jr. |
| 4,660,546 A | 4/1987 | Herrick et al. |
| 4,671,273 A | 6/1987 | Lindsey |
| 4,722,350 A | 2/1988 | Armeniades et al. |
| 4,729,373 A | 3/1988 | Peyman |
| 4,770,654 A | 9/1988 | Rogers et al. |
| 4,791,927 A | 12/1988 | Menger |
| 4,846,172 A | 7/1989 | Berlin |
| 4,876,250 A | 10/1989 | Clark |
| 4,925,299 A | 5/1990 | Meisberger et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Mueller |
| 5,129,895 A | 7/1992 | Vassiliadis et al. |
| 5,254,112 A | 10/1993 | Sinofsky et al. |
| 5,273,056 A | 12/1993 | McLaughlin et al. |
| 5,300,020 A | 4/1994 | L'Esperance, Jr. |
| 5,359,685 A | 10/1994 | Waynant et al. |
| 5,360,399 A | 11/1994 | Stegmann |
| 5,371,078 A | 12/1994 | Clark et al. |
| 5,607,966 A | 3/1997 | Hellberg et al. |
| 5,643,250 A | 7/1997 | O'Donnell, Jr. |
| 5,657,760 A | 8/1997 | Ying et al. |
| 5,698,545 A | 12/1997 | Clark et al. |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,103 A | 8/1998 | Schwartz et al. |
| 5,811,453 A | 9/1998 | Yanni et al. |
| 5,865,831 A | 2/1999 | Cozean et al. |
| 5,885,279 A | 3/1999 | Bretton |
| 5,895,831 A | 4/1999 | Brasier et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,059,772 A | 5/2000 | Hsia et al. |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,251,103 B1 | 6/2001 | Berlin |
| 6,297,228 B1 | 10/2001 | Clark |
| 6,398,809 B1 | 6/2002 | Hoffmann et al. |
| 6,450,984 B1 | 9/2002 | Lynch et al. |
| 6,494,857 B1 | 12/2002 | Neuhann |
| 6,524,275 B1 | 2/2003 | Lynch et al. |
| 6,638,239 B1 * | 10/2003 | Bergheim ............. A61F 9/0017 604/27 |
| 7,018,376 B2 | 3/2006 | Webb et al. |
| 7,125,119 B2 | 10/2006 | Farberov |
| 7,133,137 B2 | 11/2006 | Shimmick |
| 7,431,710 B2 | 10/2008 | Tu et al. |
| 8,123,729 B2 | 2/2012 | Yamamoto et al. |
| 8,540,659 B2 * | 9/2013 | Berlin ....................... A61F 2/14 604/8 |
| 8,679,089 B2 | 3/2014 | Berlin |
| 9,603,741 B2 | 3/2017 | Berlin et al. |
| 9,642,746 B2 | 5/2017 | Berlin et al. |
| 2002/0013572 A1 | 1/2002 | Berlin |
| 2002/0072673 A1 | 6/2002 | Yamamoto et al. |
| 2002/0082591 A1 | 6/2002 | Haefliger |
| 2002/0111608 A1 | 8/2002 | Baerveldt et al. |
| 2002/0165522 A1 | 11/2002 | Holmen et al. |
| 2003/0014092 A1 | 1/2003 | Neuhann |
| 2003/0105456 A1 | 6/2003 | Lin |
| 2003/0109907 A1 | 6/2003 | Shadduck |
| 2003/0175324 A1 | 9/2003 | Robinson et al. |
| 2003/0212387 A1 | 11/2003 | Kurtz et al. |
| 2003/0236483 A1 | 12/2003 | Ren |
| 2004/0070761 A1 | 4/2004 | Horvath et al. |
| 2004/0082939 A1 | 4/2004 | Berlin |
| 2004/0092856 A1 | 5/2004 | Dahan |
| 2004/0116909 A1 | 6/2004 | Neuberger et al. |
| 2004/0199149 A1 | 10/2004 | Myers et al. |
| 2004/0228013 A1 | 11/2004 | Goldstein et al. |
| 2005/0043722 A1 | 2/2005 | Lin |
| 2005/0165386 A1 | 7/2005 | Kurtz et al. |
| 2005/0240168 A1 | 10/2005 | Neuberger et al. |
| 2005/0245916 A1 | 11/2005 | Connor |
| 2005/0279369 A1 | 12/2005 | Lin |
| 2006/0021623 A1 | 2/2006 | Miller et al. |
| 2006/0050229 A1 | 3/2006 | Farberov |
| 2006/0084954 A1 | 4/2006 | Zadoyan et al. |
| 2006/0106370 A1 | 5/2006 | Baerveldt et al. |
| 2006/0114469 A1 | 6/2006 | Horvath et al. |
| 2006/0129141 A1 | 6/2006 | Lin |
| 2006/0155265 A1 | 7/2006 | Juhasz et al. |
| 2006/0195078 A1 | 8/2006 | Webb et al. |
| 2006/0200113 A1 | 9/2006 | Haffner et al. |
| 2006/0224146 A1 | 10/2006 | Lin |
| 2006/0259021 A1 | 11/2006 | Lin |
| 2007/0093794 A1 | 4/2007 | Wang et al. |
| 2007/0093796 A1 | 4/2007 | Raksi et al. |
| 2007/0121120 A1 | 5/2007 | Schachar |
| 2007/0173791 A1 | 7/2007 | Raksi |
| 2007/0208325 A1 | 9/2007 | Kurtz et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2008/0027519 A1 | 1/2008 | Guerrero |
| 2008/0058777 A1 | 3/2008 | Kurtz et al. |
| 2008/0082078 A1 | 4/2008 | Berlin |
| 2008/0082088 A1 | 4/2008 | Kurtz et al. |
| 2008/0091224 A1 | 4/2008 | Griffis, III |
| 2008/0119827 A1 | 5/2008 | Kurtz et al. |
| 2008/0278687 A1 | 11/2008 | Somani |
| 2009/0118716 A1 | 5/2009 | Brownell |
| 2009/0118717 A1 | 5/2009 | Brownell et al. |

(56) References Cited

U.S. PATENT DOCUMENTS

| | | | |
|---|---|---|---|
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0157062 A1 | 6/2009 | Hauger et al. |
| 2009/0171327 A1 | 7/2009 | Kurtz et al. |
| 2009/0281530 A1 | 11/2009 | Korn |
| 2010/0036488 A1 | 2/2010 | De, Jr. |
| 2010/0324543 A1 | 12/2010 | Kurtz et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2012/0283557 A1 | 11/2012 | Berlin |
| 2014/0288485 A1 | 9/2014 | Berlin |
| 2015/0080783 A1* | 3/2015 | Berlin ............ A61F 9/00781 604/8 |
| 2015/0305939 A1 | 10/2015 | Vera et al. |
| 2015/0305940 A1 | 10/2015 | Vera et al. |
| 2015/0313759 A1 | 11/2015 | Vera et al. |
| 2016/0095751 A1 | 4/2016 | Berlin |
| 2017/0202708 A1 | 7/2017 | Berlin |

FOREIGN PATENT DOCUMENTS

| | | |
|---|---|---|
| WO | WO-9117793 A1 | 11/1991 |
| WO | WO-9620742 A1 | 7/1996 |
| WO | WO-9901063 A1 | 1/1999 |
| WO | WO-9945868 A1 | 9/1999 |
| WO | WO-0013627 A1 | 3/2000 |
| WO | WO-0067687 A1 | 11/2000 |
| WO | WO-0067687 A1 | 11/2000 |

OTHER PUBLICATIONS

Berlin, et al. Goniophotoablation: excimer laser glaucoma filtering surgery. Lasers Light Ophthalmol 2 (1988): 17-24.
Berlin, et al. Laser sclerostomy. The state of the art. Ophthalmol Clin North Am 6 (1993): 415-424.
Berlin, et al. Perspectives on new laser techniques in managing glaucoma. Ophthalmol Clin North Am 8 (1995): 341-363.
Berlin, M. Laser Therapy. In Becker-Shaffer's Diagnosis and Therapy of the Glaucomas. 1999:521-554.
Berlin M.D., M., "Photoablation—The Basis of Photochemical Laser Interactions," Ophthalmic Lasers: A Second Genreation, Edited by W. March M.D., 1990, pp. 85-91.
Berson, M.D., F.G., et al. "Obstruction of Aqueous Outflow by Sodium Hyaluronate in Enucleanted Human Eyes" American Journal of Ophthalmology, vol. 95, No. 5, 1983, pp. 668-672.
Brown M.D., R.H., et al. "Ab Interne Filtering Surgery Internal Sclerectomy with the Trabecuphine," Opthamology Clinics of North America, vol. 1, No. 2, Dec. 1988, pp. 199-207.
Cimberle, M. "Erbium Laser Cataract Surgery is Now Bimanual, Easier and Safer to Perform" Ocular Surgery News, Aug. 2000, 3 pages.
"Customized Ablation: The Wave Continues to Move Forward", Medical Laser Report, vol. 15, No. 12, Dec. 2001, pp. 4-5.
Dietlein, et al. Ab interno infrared laser trabecular ablation: preliminary short-term results in patients with open-angle glaucoma. Graefe's archive for clinical and experimental ophthalmology 235.6 (1997): 349-353.
Dietlein, et al. Erbium: YAG laser trabecular ablation (LTA) in the surgical treatment of glaucoma. Lasers in surgery and medicine 23.2 (1998): 104-110.
Dietlein et al; "Erbium:YAG Laser Ablation on Human Trabecular Meshwork by Contact Delivery Endoprobes"; Ophthalmic Surgery and Lasers; vol. 27, No. 11; Nov. 1996; pp. 939-945.

Dietlein, et al. Morphological variability of the trabecular meshwork in glaucoma patients: implications for non-perforating glaucoma surgery.British journal of ophthalmology 84.12 (2000): 1354-1359.
E. L'Esperance.Jr.. M.D.. "Ophthalmic Lasers Photocoagulation, Photoradiation. and Surgery," The C.V. Mosby Company, 1983 pp. 529-554.
Fankhauser, et al. Optical principles related to optimizing sclerostomy procedures. Ophthalmic Surgery, Lasers and Imaging Retina 23.11 (1992): 752-761.
Final Office Action received for U.S. Appl. No. 09/860,842, dated Dec. 15, 2006 , 8 pages.
Final Office Action received for U.S. Appl. No. 09/860,842, dated Dec. 30, 2009 , 16 pages.
Final Office Action received for U.S. Appl. No. 09/860,842, dated Jan. 9, 2006 , 5 pages.
Final Office Action received for U.S. Appl. No. 09/860,842, dated Jul. 7, 2014, 16 pages.
Final Office Action received for U.S. Appl. No. 09/860,842, dated Nov. 24, 2008, 10 pages.
Final Office Action received for U.S. Appl. No. 10/640,464, dated Feb. 17, 2010, 12 pages.
Final Office Action received for U.S. Appl. No. 10/640,464, dated Jul. 17, 2014, 13 pages.
Final Office Action received for U.S. Appl. No. 10/640,464, dated Jul. 31, 2006, 7 pages.
Final Office Action received for U.S. Appl. No. 10/640,464, dated Nov. 24, 2008, 7 pages.
Final Office Action received for U.S. Appl. No. 10/640,464, dated Oct. 17, 2007, 5 pages.
Final Office Action received for U.S. Appl. No. 11/874,179, dated Apr. 4, 2011, 24 pages.
Final Office Action received for U.S. Appl. No. 11/874,179, dated Jan. 14, 2010, 24 pages.
Final Office Action received for U.S. Appl. No. 11/970,488, dated Feb. 4, 2011, 10 pages.
Final Office Action received for U.S. Appl. No. 11/970,488, dated Oct. 16, 2009, 10 pages.
Hill, et al. Effects of pulse width on erbium: YAG laser photothermal trabecular ablation (LTA). Lasers in surgery and medicine 13.4 (1993): 440-446.
Hill, et al. Laser trabecular ablation (LTA). Lasers in surgery and medicine 11.4 (1991): 341-346.
Hoerauf, et al. Slit-lamp-adapted optical coherence tomography of the anterior segment. Graefe's archive for clinical and experimental ophthalmology 238.1 (2000): 8-18.
Huang, et al. Optical coherence tomography. Science (New York, NY) 254.5035 (1991): 1178-1181.
Iliev, et al. The repair response following Nd: YAG laser sclerostomy ab interno in rabbits. Experimental eye research 61.3 (1995): 311-321.
International preliminary examination report dated Sep. 19, 2002 for PCT Application No. PCT/US01/16317.
International search report dated Jul. 5, 2002 for PCT Application No. PCT/US01/16317.
Jacobi, et al. Microendoscopic trabecular surgery in glaucoma management. Ophthalmology 106.3 (1999): 538-544.
Jean et al "Noncontact photoacoustic spectroscopy during photoablation with a 193-nm excimer laser"; Ger J Ophthalmoi.;vol. 2, No. 6; Nov. 1993; pp. 404-408 (Abstract only).
Jean et al. "Noncontact photoacoustic spectroscopy during photoablation with a 193-nm excimer laser" Ger. J. Ophthalmol.; vol. 2, No. 6; Nov. 1993; pp. 404-408.
Juhasz, et al. Application of Femtosecond Laser Surgery for the Treatment of Glaucoma; in Frontiers in Optics. OSA Technical Digest (CD) (Optical Society of America, 2008).
Larson M.D. et al., "Viscoelastic Agents", The CLAO Journal, vol. 15, No. 2, Apr. 1989, 10 pp.
Latina, et al. New Lasers for Glaucoma Surgery. In Principles and Practice of Ophthalmology. Elsevier Health Sciences. 2000:600-608.

(56) References Cited

OTHER PUBLICATIONS

Lee, et al. Short-pulsed neodymium-YAG laser trabeculotomy. An in vivo morphological study in the human eye. Investigative ophthalmology & visual science 29.11 (1988): 1698-1707.
Leitgeb, et al. Spectral measurement of absorption by spectroscopic frequency-domain optical coherence tomography. Optics letters 25.11 (2000): 820-822.
L'Esperance Jr. M.D., F., "Ophthalmic Lasers Photocoagulation, Photoradiation, and Surgery," The C.V. Mosby Company, 1983, pp. 529-538, 554.
Liesegang M.D., T., 'Viscoelastics, Interactions Opthalmology Clinics, vol. 33, No. 4, 1993, pp. 127-147.
Lin, C. Ph.D. Laser-Tissue Interactions. Ophthalmology Clinics of North America, vol. 6, No. 3, Sep. 1993. pp. 381-391.
M. Berlin M.D., "New Developments in Glaucoma Laser Surgery Procedures," Ophthalmology Clinics of North America. vol. II. No. 2. Jun. 1998. pp. 187-200.
M. Vogel, G. Scheurer, W. Neu, M. Dressel, H. Gerhardt, "Die Ablation des Trabekelwerks," Klin. Mbl. Augenheilk. 197 (1990) 250-253.
Martin Vogel, Kyra Lauritzen, "Punktuelle Excimerlaserablation des Trabekelwers Klinische Ergebnisse," Opthalmologe 1997 94:665-667.
M.Berlin M.D., "Coreneal Photoblation,"Ophthalmic Lasers: A seceond Generation, Edited by March . M.d., 1990, pp. 93-104.
M.Berlin M.D., Excimer Laser Applications in Glaucona Surgery, Ophthalmology Clinics of North America, vol. 1, No. 2. Dec. 1988, pp. 255-263.
McHam, et al. Erbium: YAG laser trabecular ablation with a sapphire optical fiber. Experimental eye research 65.2 (1997): 151-155.
M.H. Vogel, P. Schildberg, "Histologische Friihergebnisse nach experimenteller Lasertrabekulopunktur," Klin. Mhl. Augenheilk. 163 (1973) 353-358.
Muller, et al. Biophysics of the photoablation process. Lasers in Medical Science 6.3 (1991): 241-254.
Nakamura, et al. Femtosecond laser photodisruption of primate trabecular meshwork: an ex vivo study. Invest Ophthalmol Vis Sci. Mar. 2009;50(3):1198-204. doi: 10.1167/iovs.07-1536. Epub Oct. 3, 2008.
Neuhann, Th et al., "Excimer Laser Trabecular Ablation ab interne (EL T) in the Treatment of Chronic Open-Angle Glaucoma" Ophthalmo-Chirurgie 13: Offprint (2001).
Non-Final Office Action received for U.S. Appl. No. 09/860,842, dated Apr. 17, 2008, 10 pages.
Non-Final Office Action received for U.S. Appl. No. 09/860,842, dated Feb. 25, 2016, 21 pages.
Non-Final Office Action received for U.S. Appl. No. 09/860,842, dated Jun. 30, 2006, 5 pages.
Non-Final Office Action received for U.S. Appl. No. 10/640,464, dated Apr. 21, 2008, 7 pages.
Non-Final Office Action received for U.S. Appl. No. 10/640,464, dated Dec. 15, 2006, 8 pages.
Non-Final Office Action received for U.S. Appl. No. 10/640,464, dated Feb. 26, 2016, 27 pages.
Non-Final Office Action received for U.S. Appl. No. 10/640,464, dated Jun. 9, 2009, 11 pages.
Non-Final Office Action received for U.S. Appl. No. 10/640,464, dated Mar. 2, 2006, 5 pages.
Non-Final Office Action received for U.S. Appl. No. 11/874,179, dated Jul. 15, 2010, 24 pages.
Non-Final Office Action received for U.S. Appl. No. 11/874,179, dated Jun. 26, 2009, 19 pages.
Non-Final Office Action received for U.S. Appl. No. 11/874,179, dated Mar. 7, 2013, 9 pages.
Non-Final Office Action received for U.S. Appl. No. 11/970,488, dated Feb. 27 2009, 8 pages.
Non-Final Office Action received for U.S. Appl. No. 11/970,488, dated Jun. 19, 2012, 18 pages.
Non-Final Office Action received for U.S. Appl. No. 13/464,949, dated Dec. 5, 2014, 23 pages.
Non-Final Office Action received for U.S. Appl. No. 14/028,460, dated Jan. 12, 2016, 9 pages.
Non-Final Office Action received for U.S. Appl. No. 14/732,627, dated Feb. 10, 2016, 17 pages.
Notice of Allowance and Fee transmittal received for U.S. Appl. No. 11/970,488, dated May 3, 2013, 10 pages.
Notice of allowance dated Dec. 19, 2016 for U.S. Appl. No. 14/028,460.
Notice of Allowance received and Fee transmittal for U.S. Appl. No. 11/874,179, dated Oct. 30, 2013, 12 pages.
Notice of Allowance received for U.S. Appl. No. 11/970,488, dated Jun. 28, 2013, 6 pages.
Office Action dated Oct. 4, 2016 for U.S. Appl. No. 09/860,842.
Office action dated Oct. 6, 2016 for U.S. Appl. No. 10/640,464.
Office Action received for U.S. Appl. No. 09/860,842, dated Dec. 8, 2003, 5 pages.
Office Action received for U.S. Appl. No. 09/860,842, dated Feb. 12, 2003, 6 pages.
Olivius M.D., E., et al., "Interocular Pressure After Cataract Surgery with Healon," American Intraocular Implant Society, vol. 11, Sep. 1985, pp. 480-482.
Owen, David. A moving-mirror gonioscope for retinal surgery. 1977. British Journal of Ophthalmology, 61, 246-247.
Radhakrishnan, et al. Real-time optical coherence tomography of the anterior segment at 1310 nm. Archives of ophthalmology 119.8 (2001): 1179-1185.
Rosencwaig, A. "Photoacoustic spectroscopy." Annual review of biophysics and bioengineering 9.1 (1980): 31-54.
Royston, et al. Comparison of the thermal tissue effects produced by aged sapphire and silica hemispherical tips. Lasers in surgery and medicine 14.1 (1994): 47-58.
Shirato et al; "Internal Sclerostomy with Argon Contact Laser—Animal Experiment Using 5-Fiuorouracil"; Japanese Journal of Ophthalmol; 34(3); 1990; 381-387.
Shirato et al; "Internal Sclerostomy with Argon Contact Laser—Animal Experiment Using 5-Fiuorouracil"; Jpn J Ophthalmol; 34(3); 1990; 381-387 (Abstract).
Taboada, J. et al., "An Extreme Sensitivity in the Corneal Epithelium to FAR UV ArF Excimer Laser Pulses," Proc. of the Sci. Prog. of the Aerospace Med. Assoc., 1981, San Antonio, TX. pp. 98-99.
Toyran, et al. Femtosecond laser photodisruption of human trabecular meshwork: an in vitro study. Exp Eye Res. Sep. 2005;81(3):298-305.
Translated Article: Punktuelfe Excimerlaserablation des Trabekelwerks Klinische Ergebnisse (Punctual Excimer Laser Ablation of trabecular meshwork Clinical results) by Lauritzen and Vogel; Opthalmologe 1997 94:665-667.
Translation, "Showing translation for the ablation of the trabecular meshwork . . . " M. Vogel, G. Scheurer, W Neu, M. Dressel, H. Gerhardt; Klin. Mbl. Augenheilk. 197 (1990) 250-253.
Translation of M.H. Vogel, P. Schildberg, "[Histological findings afer experimental laser-trabecula-puncture {authors transl)]," Klin. Monbl Augenheilkd 1973, 163(3): 353-358.
Trokel M.D., S. et al., "Excimer Laser Surgery of the Cornea," American Journal of Ophthalmology, vol. 96, Dec. 1983, pp. 710-715.
Verdaasdonk, R.M., et al., "Ray Tracing of Optically Modified Fiber Tips 1: Spherical Probes," Applied Optics, vol. 30, No. 16, Jun. 1991, pp. 2159-2171.
Verdaasdonk, R.M., et al., "Ray Tracing of Optically Modified Fiber Tips 2: Laser Scalpels" Applied Optics, vol. 30, No. 16, Jun. 1991, pp. 2172-2177.
Wolbarsht, M., "Laser Surgery: C02 or HF," Journal of Quantum Electronics, vol. QE20, No. 12, Dec. 1984, pp. 1427-1432.
"detector". Macmillan Online Dictionary.<http://www.macmillandictionary.com/dictionary/american/detector>.
"detector". Oxford Dictionaries Online.<http://www.oxford-dictionaries.com/definition/detector>.
"sensor."Cambridge Advanced Learner's Dictionary. Cambridge Dictionaries Online.<http://dictionary.cambridge.org/define.asp?dict=CALD&key=71811>.

(56) References Cited

OTHER PUBLICATIONS

"sensor."Compact Oxford English Dictionary. AskOxford.com. <http://www.askoxford.com/concise_oed/sensor?view=uk>.
Fercher et al., Complex Spectral Interferometry OCT, Proc. SPIE 3564, EUROPTO Conference on Lasers in Ophthalmology, Stockholm Sweden, Sep. 1998.
MLase AG. Specifications ExTra—Laser for Glaucoma treatment. Jul. 13, 2012.
MLase AG. Specifications FIDO—Laser for ExTra Laser system. Jul. 13, 2012.
Notice of allowance dated Mar. 16, 2017 for U.S. Appl. No. 14/191,277.
Office action dated May 5, 2017 for U.S. Appl. No. 10/640,464.
Office action dated Feb. 3, 2017 for U.S. Appl. No. 14/191,277.
Office Action dated May 4, 2017 for U.S. Appl. No. 09/860,842.

\* cited by examiner

DELIVERY SYSTEM AND METHOD OF USE FOR THE EYE

RELATED APPLICATIONS

This application is a continuation of U.S. patent application Ser. No. 14/028,460, filed Sep. 16, 2013, which is a continuation of U.S. patent application Ser. No. 11/970,488, filed Jan. 7, 2008, now U.S. Pat. No. 8,540,659, which is a divisional of U.S. patent application Ser. No. 09/860,842, filed May 21, 2001, which claims the benefit of U.S. Provisional Application No. 60/205,846, filed May 19, 2000, all of which are incorporated herein by reference.

FIELD OF THE INVENTIONS

This invention relates to devices and methods for treatment of human tissues, especially interior human tissue structures in the eye for restructuring, and more particularly to treatment of glaucoma.

BACKGROUND

Glaucoma, a serious long-term health care problem, is a disorder of the eye in which elevated intraocular pressure ultimately leads to damage to the optic nerve and to blindness. Glaucoma has been cited as the second most common cause of blindness affecting several million people in the United States alone.

In order to fully appreciate the present invention, a brief overview of the anatomy of the eye is provided. As schematically shown in FIG. 1, the outer layer of the eye includes a sclera 17 that serves as a supporting framework for the eye. The front of the sclera includes a cornea 15, a transparent tissue that enables light to enter the eye. An anterior chamber 7 is located between the cornea 15 and a crystalline lens 4. The anterior chamber 7 contains a constantly flowing clear fluid called aqueous humor 1. The crystalline lens 4 is connected to the eye by fiber zonules, which are connected to the ciliary body 3. In the anterior chamber 7, an iris 19 encircles the outer perimeter of the lens 4 and includes a pupil 5 at its center. The pupil 5 controls the amount of light passing through the lens 4. A posterior chamber 2 is located between the crystalline lens 4 and the retina 8.

As shown in FIG. 2, the anatomy of the eye further includes a trabecular meshwork 9, which is a narrow band of spongy tissue that encircles the iris 19 within the eye. The trabecular meshwork has a variable shape and is microscopic in size. It is of a triangular cross-section and of varying thickness in the range of 100-200 microns. It is made up of different fibrous layers having micron-sized pores forming fluid pathways for the egress of aqueous humor. The trabecular meshwork 9 has been measured to about a thickness of about 100 microns at its anterior edge, Schwalbe's line 18, which is at the approximate juncture of the cornea 15 and sclera 17.

The trabecular meshwork widens to about 200 microns at its base where it and iris 19 attach to the scleral spur. The passageways through the pores in trabecular meshwork 9 lead through very thin, porous tissue called the juxtacanalicular trabecular meshwork 13 that in turn abuts the interior side of a structure called Schlemm's canal 11. Schlemm's canal 11 is filled with a mixture of aqueous humor and blood components and branches off into collector channels 12 which drain the aqueous humor into the venous system. Because aqueous humor is constantly produced by the eye, any obstruction in the trabecular meshwork, the juxtacanalicular trabecular meshwork or in Schlemm's canal prevents the aqueous humor from readily escaping from the anterior eye chamber which results in an elevation of intraocular pressure within the eye.

As shown in FIG. 2, the eye has a drainage system for the draining aqueous humor 1 located in the corneoscleral angle. In general, the ciliary body 3 produces the aqueous humor 1. This aqueous humor flows from the posterior chamber 2 through the pupil 5 into the anterior chamber 7 to the trabecular meshwork 9 and into Schlemm's canal 11 to collector channels 12 to aqueous veins. The obstruction of the aqueous humor outflow which occurs in most open angle glaucoma (i.e., glaucoma characterized by gonioscopically readily visible trabecular meshwork) typically is localized to the region of the juxtacanalicular trabecular meshwork 13, which is located between the trabecular meshwork 9 and Schlemm's canal 11, more specifically, the inner wall of Schlemm's canal. It is desirable to correct this outflow obstruction by enhancing the eye's ability to use the inherent drainage system.

When an obstruction develops, for example, at the juxtacanalicular trabecular meshwork 13, intraocular pressure gradually increases over time. Therefore, a goal of current glaucoma treatment methods is to prevent optic nerve damage by lowering or delaying the progressive elevation of intraocular pressure. Many have searched for an effective method of lowering and controlling intraocular pressure. In general, various pharmaceutical treatments have been employed to control intraocular pressure. While these treatments may be effective for a period of time, the intraocular pressure in the diseased eyes often increases in many patients. The most frequent problems result from patients failing to follow their treatment regimen thus causing inadequately controlled glaucoma, which results in irreversible damage to the optic nerve that ultimately results in vision loss.

After a trial of pharmaceutical treatments fails to stop the progression of elevated intraocular pressure, or in some cases as primary therapy, a surgical treatment method or procedure is generally performed on the eyes of the patients. The human eye is a particularly challenging target for corrective surgery because of the size, fragility, distribution and characteristics of interior tissues. Surgical attempts to lower the intraocular pressure include various therapies that generally fall under the name "glaucoma filtering surgery".

The surgical therapies in current use, however, do not address the location of the outflow obstruction that is recognized for causing the elevated intraocular pressure. These procedures include mechanically cutting portions of the eye anatomy and are known by such names as trabeculectomy, trabeculotomy, goniotomy and goniocurettage. Significantly, these techniques have been found to be unsuccessful for long term intraocular pressure control. Trabeculectomy has been the most popular procedure in glaucoma surgery in which an opening is created in the sclera to enable aqueous humor to drain into channels external to the eye globe. This procedure, however, has many complications including leaks, infections, hypotony (e.g., low eye pressure), and requirements for post-operative needling, undesirable antimetabolite use, a need for flap suture adjustment to maintain the function of the opening and a need for long-term monitoring to avoid late complications. Another procedure, called deep sclerectomy, attempts to create an intrascleral filtration pocket, but does not alter anatomic relationships and does not treat the region of outflow obstruction. Another procedure, called viscocanalostomy, does attempt to alter the outflow obstruction between Schlemm's canal and the porous juxtacanalicular layer. In viscocanalostomy, an opening via the sclera is created in an attempt to localize and insert a tube into Schlemm's canal without puncturing the trabecular meshwork. Schlemm's canal is dilated by injection of viscoelastic materials into the canal. By altering the juxtacanalicular meshwork's anatomic relationships, an increased aqueous outflow results. Although attempting to address the outflow obstruction that causes the increased intraocular pressure, viscoanalostomy has not been shown to be successful. Thus, a new effective treatment method was needed for glaucoma to address the outflow obstruction that causes elevated intraocular pressure.

In the prior art, lasers have been used to treat glaucoma. Specifically, lasers have been used to thermally modify and/or to puncture completely through various structures, including the trabecular meshwork, Schlemm's canal and the sclera. Moreover, lasers have been used in attempts to open the anterior chamber to an internal outflow rather than an external outflow channel, or reservoir. Early attempts utilized the lasers available at that time which included Q-switched ruby lasers, neodymium:yttrium aluminum garnet (Nd:YAG) lasers, and argon lasers. These procedures had many names: laser trabeculopunture, laseropuncture, goniopuncture, laser trabeculostomy, laser trabeculotomy, and lager trabeculoplexy. The above described procedures attempted to remove or move or alter portions of the trabecular meshwork. The procedures have several shortcomings. First, they have limited ability to lower the intraocular pressure to a desirable level. Second, while most found initial success in creating a puncture through the meshwork, the short duration of the reduced intraocular pressure proved to be ineffective in treating the long term effects of glaucoma. As a result, patients suffered undesirable additional post operative procedures to lower the intraocular pressure and required continuous long-term monitoring. The short duration of the reduced pressure has been linked to the body's subsequent inflammatory healing response at the openings created in the eye. The trauma associated with the shearing and tearing of the tissues and the thermal tissue damage caused by the above procedures initiates wound-healing processes which tend, with time, to reseal the created openings.

These early laser procedures failed in that no consideration was given to the size of the openings in the trabecular meshwork. In addition, these procedures also failed to recognize the importance of reducing collateral tissue damage surrounding the created hole. It has been seen that large areas of surrounding tissue damage invite greater inflammation that results in a greater healing response. In addition, if damage occurs to the outer wall of Schlemm's canal and collector channel openings, resultant scarring prevents aqueous humor egress through the distal outflow pathways and effectively eliminates any benefit of the attempted procedure. The actual and potential thermal effect produced by the lasers is a significant contributing factor to the resultant tissue damage. Therefore, the opening size and tissue damage needs to be controlled by controlling the thermal trauma to the target tissues.

SUMMARY

The present invention is an improved glaucoma treatment by providing a method and delivery system for creating an aqueous outflow pathway through the trabecular meshwork, juxtacanalicular trabecular meshwork and Schlemm's canal of an eye in order to reduce elevated intraocular pressure. The method includes the steps of introducing a fiber-optic probe between the outer surface of the eye and the anterior chamber until a distal end of the fiber-optic probe is in contact with or adjacent to a target site including the trabecular meshwork, the juxtacanalicular trabecular meshwork and Schlemm's canal distal to the meshwork. Pulsed laser radiation is delivered from the distal end of the fiber-optic probe sufficient to cause photoablation of the juxtacanalicular trabecular meshwork and an inner wall of Schlemm's canal in the target tissues. The fiber-optic probe may be stationery or advanced creating an aperture through these tissues to enable and improve fluid flow from the anterior chamber of the eye. The pulsed radiation is delivered in wavelengths, pulse durations and fluences to cause a minimal thermal effect on the tissue while removing and modifying tissue.

In a second aspect of the invention, a method of controlling an interior anatomy of an eye during an intraocular procedure includes the steps of creating an opening in the eye, and filling the anterior chamber of the eye through the opening with a viscoelastic material. The interior pressure within the eye may be sensed with a pressure sensor. The interior pressure may be adjusted by controlling the amount of viscoelastic material so as to compress or decompress the interior anatomy of the eye at a predetermined target anatomy site. In one aspect, the interior anatomy includes the trabecular meshwork. Viscoelastic materials of various viscosities and other protective agents placed within structures enable micro-manipulation of such structures for surgical modification while protecting adjacent structures from possible damage. Schlemm's canal may be inflated to enable perforation of the inner wall while protecting the outer wall structures.

In a third aspect of the invention, a method of reducing intraocular pressure in an eye is provided by creating an aqueous flow pathway through the trabecular meshwork and the inner wall of Schlemm's canal in which an implant device is inserted into the aqueous flow pathway and serves as a conduit to remove aqueous humor. The implant device may extend from the anterior chamber of the eye or the trabecular meshwork to the inner wall or lumen of Schlemm's canal.

In a fourth aspect of the invention, an apparatus provides laser energy to target tissues of an eye. The apparatus includes a laser unit for generating laser energy, and a delivery system that includes a laser probe. The laser probe includes an optical fiber core for transmitting laser energy from a distal end to target tissues of the eye, and a proximal end for coupling to the laser unit and may include sensing devices which generate and receive signals to enable a controller. In one embodiment, the sensing device features a sensor for sensing the temperature in the eye and at the target tissues before, during and after photoablation of the target tissues. In another embodiment, the sensing device has a sensor for sensing the laser probe relationship to the target tissues. In a further embodiment, the sensing device has a sensor for sensing the pressure both within the eye and at the probe/target tissues. A servo feedback mechanism may utilize sensed pressure to provide a controlled adjustment of the treatment parameters.

In a fifth aspect of the invention, a device for reducing and maintaining reduced intraocular pressure is implanted into at least an inner wall of Schlemm's canal or adjacent trabecular meshwork. The device may include a tubular portion having a distal end including a first engaging member for attaching to the interior surface of the proximal inner wall of Schlemm's canal or adjacent trabecular meshwork. The tubular portion includes a proximal end having a plurality of second engaging members for attaching to the trabecular meshwork.

BRIEF DESCRIPTION OF THE DRAWINGS

The foregoing summary of the invention, as well as the following detailed description of the preferred embodiments is better understood when read in conjunction with the accompanying drawings, which are included by way of example, and not by way of limitation with regard to the claimed invention, wherein:

DETAILED DESCRIPTION

Figure 3:
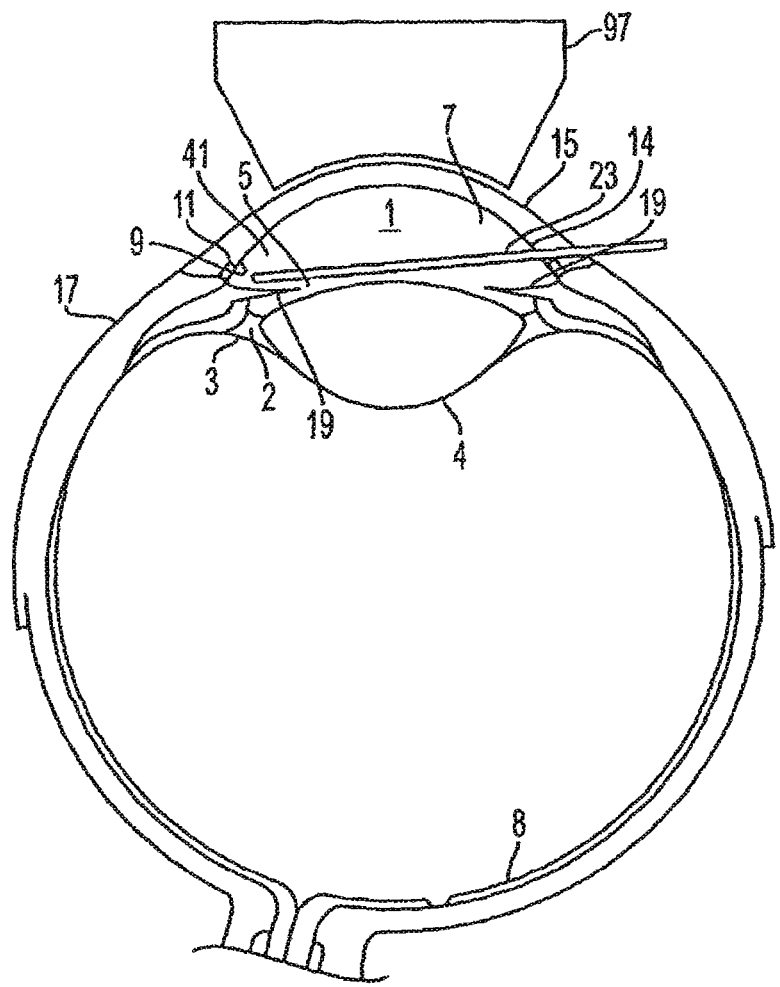
FIG. 3 is schematic sectional view of an eye illustrating a fiber-optic probe disposed next to the trabecular meshwork in the anterior chamber of the eye.
Figure 4:
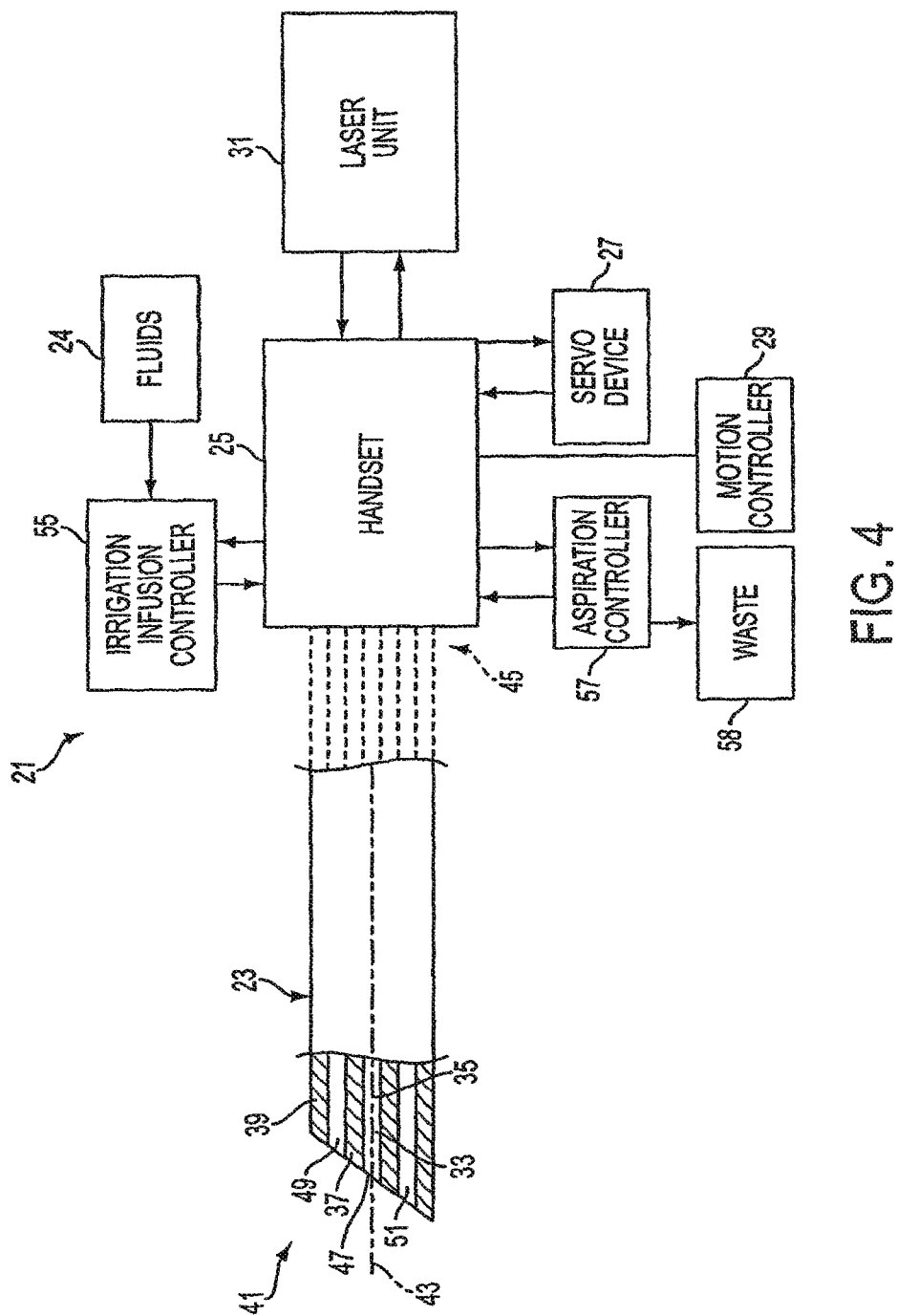
FIG. 4 is a schematic diagram of an embodiment of a laser delivery system including a side-sectional fragmentary view of the operative end of a fiber-optic probe

FIGS. 3-12 illustrate an embodiment of a laser delivery system 21 for micromachining, microscupting, or microshaping the interior anatomy of an eye. As shown in FIG. 4, a laser delivery system 21 may be operated to reduce the thermal component of laser energy contributing to collateral tissue damage. As further shown in FIG. 4, laser delivery system 21 includes a fiber-optic probe 23 for entering the eye and removal or manipulation of eye tissue. Fiber-optic probe 23 is mechanically and electrically coupled to a probe handset 25. Probe handset 25 includes controls for manipulating and operating the fiber-optic probe. A servo device 27 is connected to fiber-optic probe 23 for automatically controlling pressure within the eye during an intraocular procedure. If desired, a motion controller 29 may selectively automate transocular movement of fiber-optic probe 23 into a desired site for tissue removal and/or manipulation. A laser unit 31 provides laser energy in the form of wavelength pulses through fiber optic probe 23 for tissue removal from the interior of the eye by photoablation. Photoablation is the process of removing surface tissues, typically via laser energy, with minimal thermal transfer to the remaining tissues.

Figure 13:
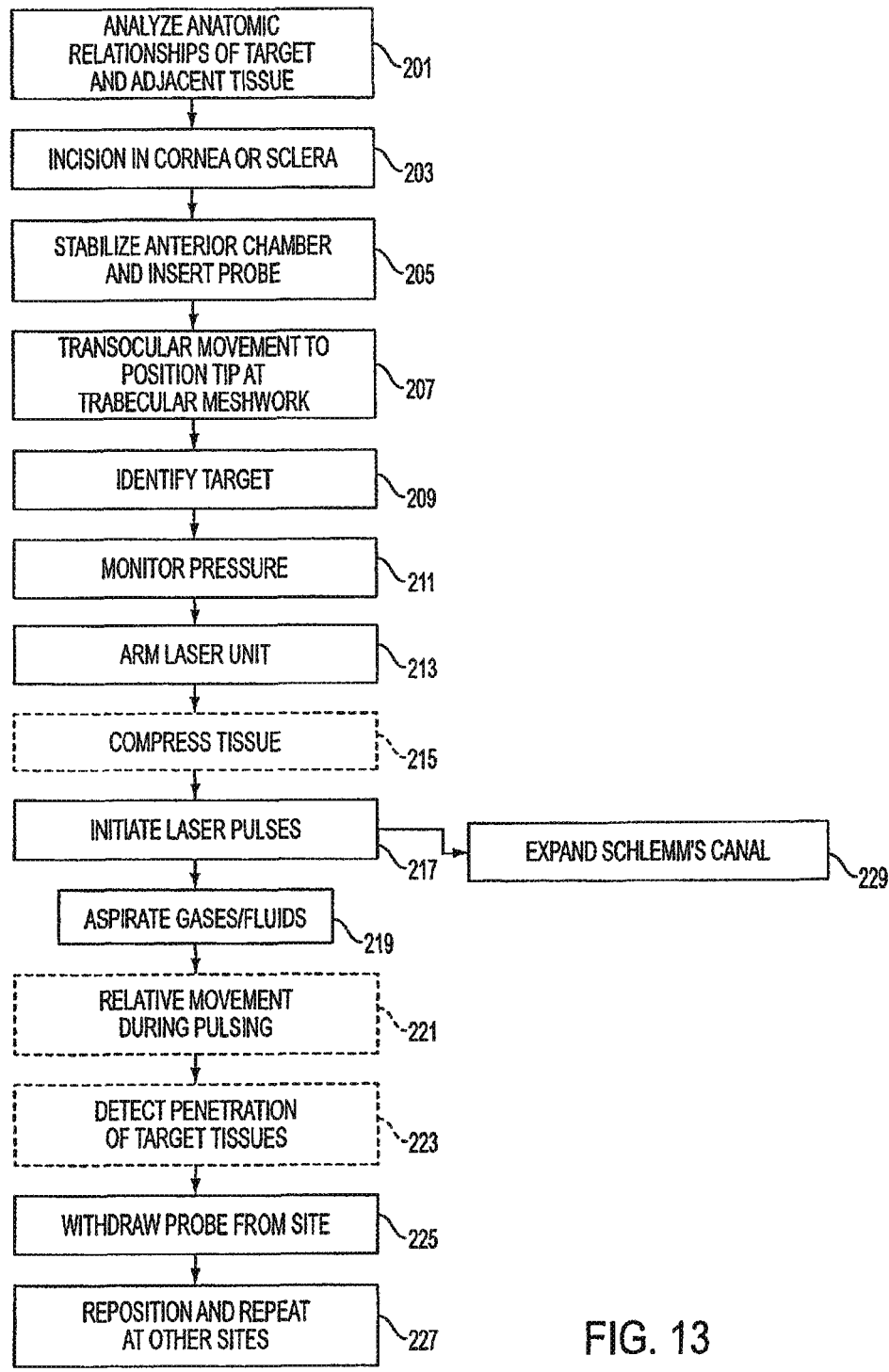
FIG. 13 is a block diagram of an embodiment of a method of treating glaucoma with a laser delivery system.

Referring to FIGS. 3 and 13, an overview of a manner of operating laser delivery system 21 for treatment of glaucoma or other eye conditions follows. FIG. 3 is a side sectional view of the interior anatomy of a human eye showing fiber-optic probe 23 in relation to treating glaucoma. After applying local and/or retrobular anesthesia to eliminate pain, a small self-sealing incision 14 is created in the cornea 15 with a surgical blade or other device. The anterior chamber is stabilized with a viscoelastic agent. Fiber-optic probe 23 is positioned and advanced in the incision 14 into the anterior chamber 7 until a distal end of fiber-optic probe 23 contacts or is adjacent to the desired target tissues for removal. Laser energy produced by laser unit 31 is delivered from the distal end of fiber-optic probe 23 in contact or adjacent to the tissues sufficient to cause photoablation of tissues which may include the trabecular meshwork 9, the juxtacanalicular trabecular meshwork 13 and an inner wall of Schlemm's canal 11 as the target tissues. Fiber optic probe 23 may be advanced towards Schlemm's canal 11 and creates an aperture in the proximal inner wall of Schlemm's canal 11, but does not perforate the distal outer wall. If desired, additional apertures may be created in the trabecular meshwork and target tissues. Thus, the resultant aperture or apertures restore the natural drainage system for the aqueous humor.

Referring to FIG. 4, fiber-optic probe 23 is illustrated having similar structure as structure disclosed in U.S. Pat. No. 4,846,172 to the present inventor, which is herein fully incorporated by reference. Probe 23 includes an axially disposed light transmitting core 33 having an optical fiber or a plurality of optical fibers 35 in which core 33 is stiffened by an encapsulating sheath 37. The diameter of a single optical optical fiber 35 should be sufficiently large to transmit sufficient light energy for causing photoablation of target tissues and are typically in a range from 4-6 microns. A single optical fiber or a plurality of optical fibers 35 may be used in a bundle of a diameter ranging from 100 to 1000 microns. Core 33 and sheath 37 are encased within an outer metal sleeve or shield 39 that is typically constructed of stainless steel. The outer diameter of sleeve 39 is preferably no larger than 1000 microns. If desired, the diameter may be as small as 100 microns, when smaller optical fibers are implemented with laser delivery system 21. If desired, the sleeve may be flexible so that it can be bent or angled.

The tip or distal end 41 of probe 23 may be inclined with respect to a central longitudinal axis 43 extending between distal end 41 and a proximal end 45 of the probe. The angle of the inclination is preferably about 45 degrees and may range from 0 to 180 degrees. The inclined geometry orients the distal end 41 of probe 23 relative to the surface of the target tissues so that photoablative decomposition of target tissues proceeds uniformly and so that distal end 41 of probe 23 is oriented to enable photoablation of the target tissues.

Figure 5A:
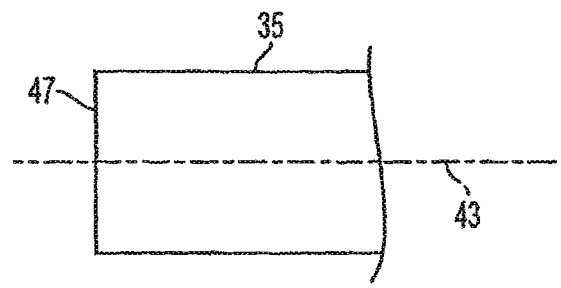
FIGS. 5A-5F are schematic diagrams of alternative embodiments of a tip of a fiber-optic probe.
Figure 5B:
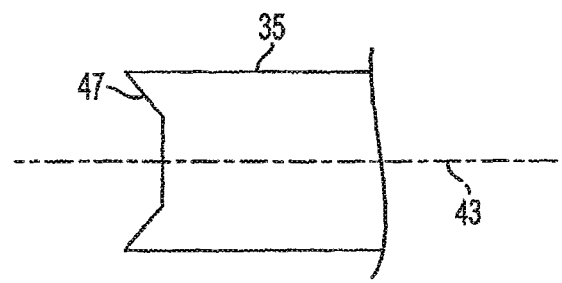
Figure 5C:
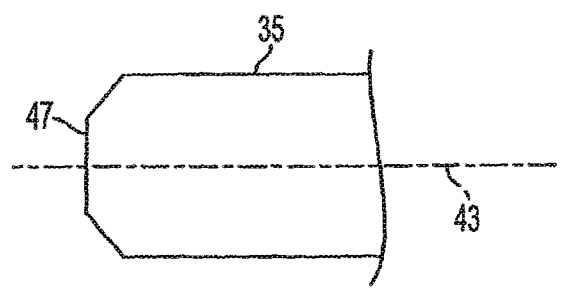
Figure 5D:
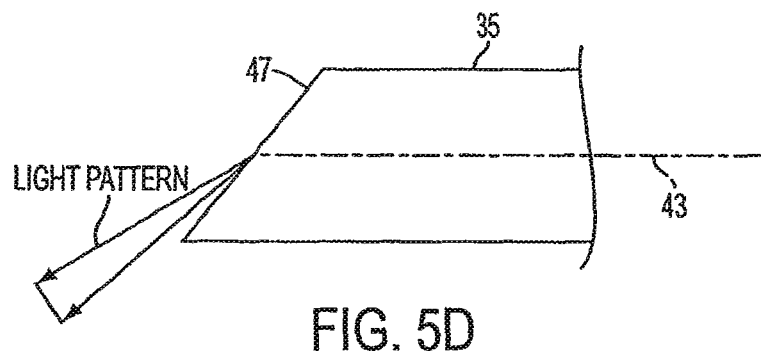
Figure 5E:
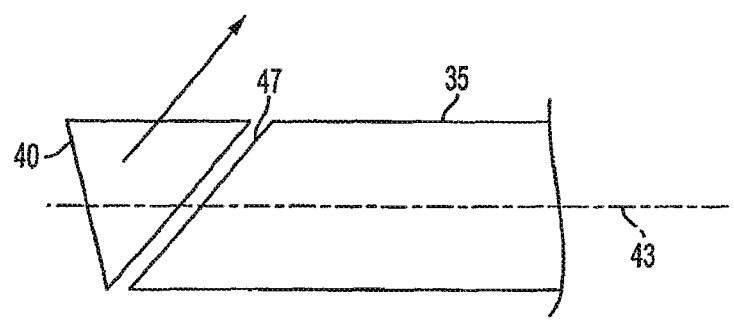
Figure 20A:
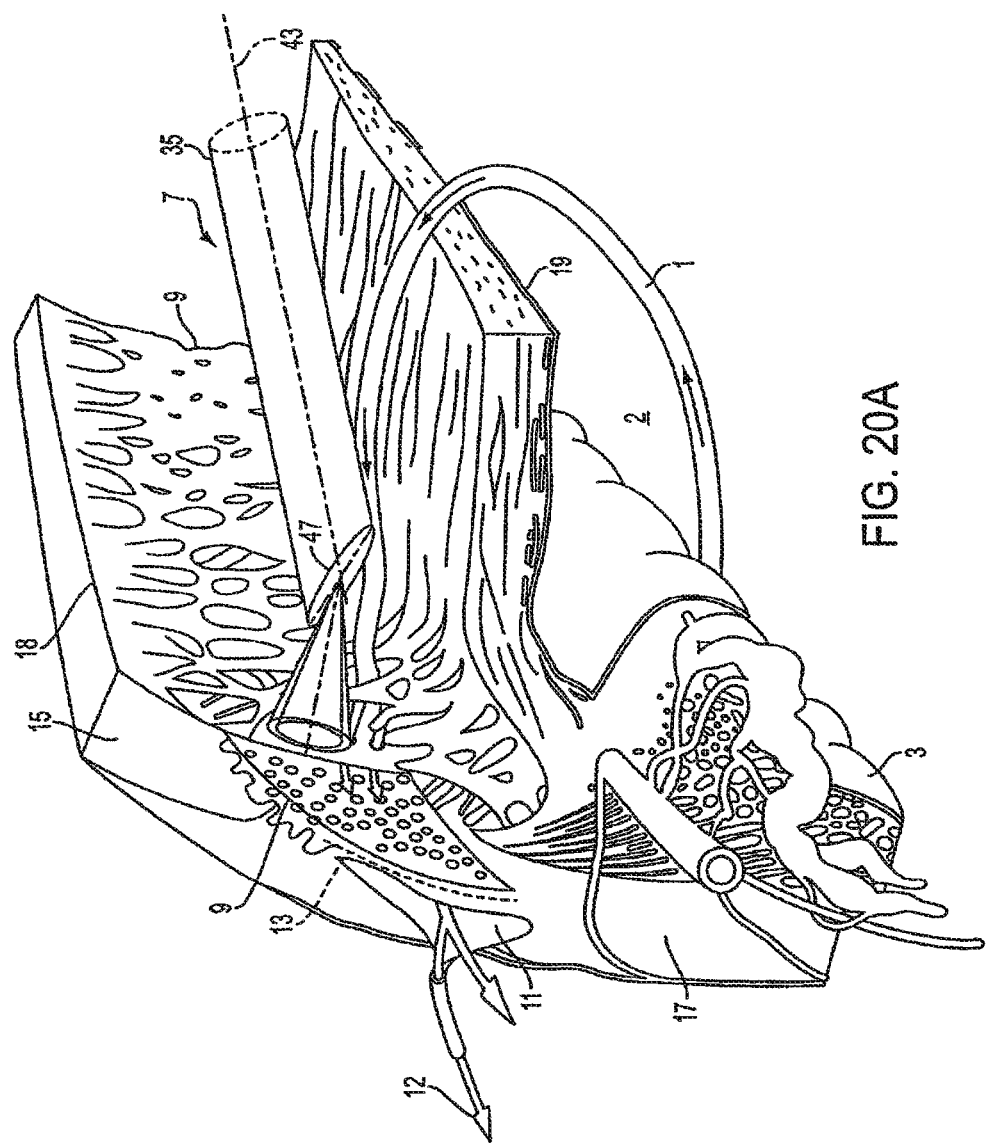
FIGS. 20A-20B are schematic diagrams of a beveled face fiber-optic tip photoablating target tissues.
Figure 20B:
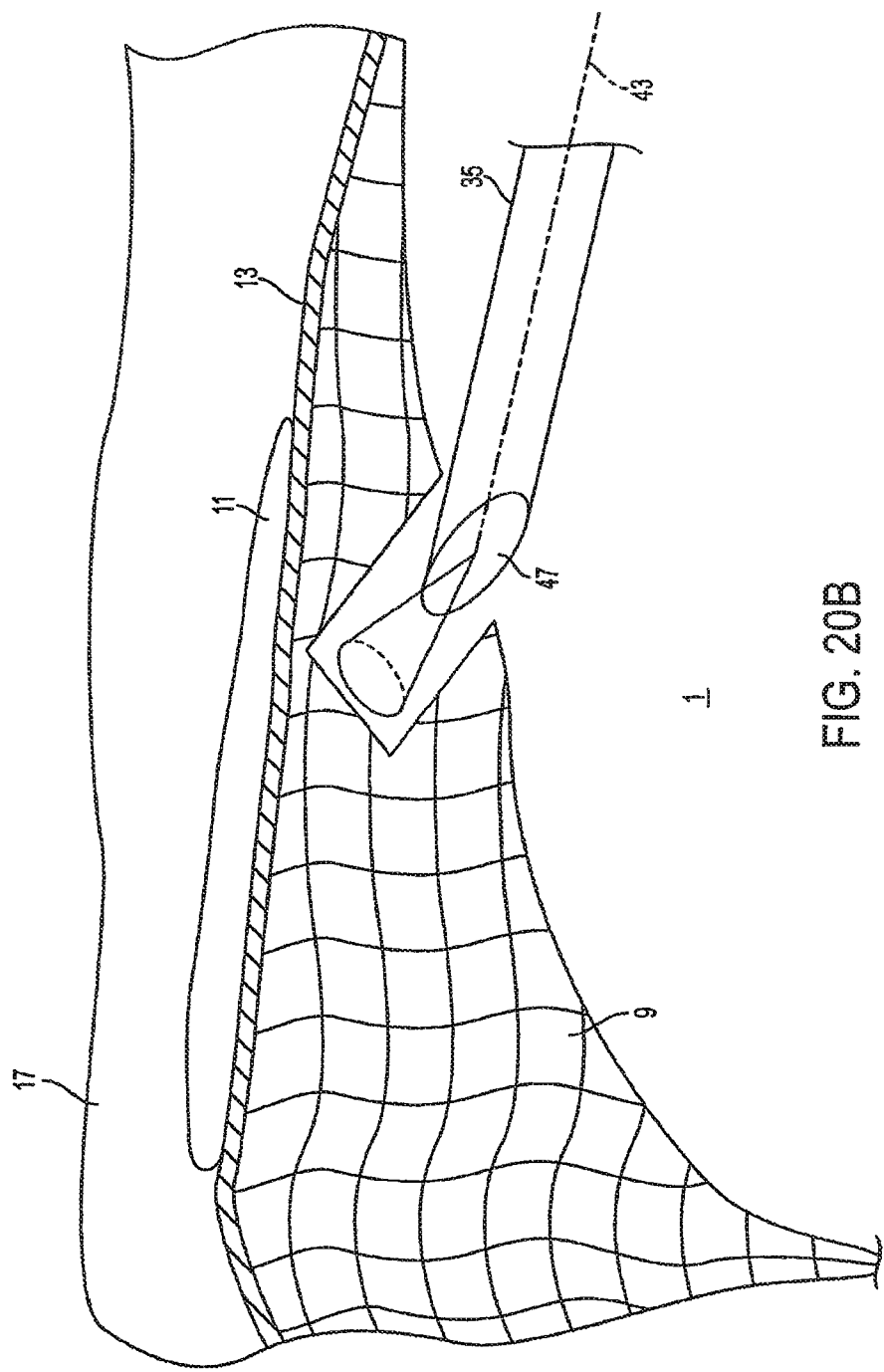

The tip 47 of the optical fiber or fibers 35 emanates light with controlled divergence so that a laser spot size encompasses a larger target area than the fiber cross sectional diameter. This enables perforations in target tissues to have a larger diameter than the probe sleeve 39 and also reduces thermal tissue damage. Generally, tip 47 of the optical fiber or fibers 35 is shaped such that each tip has a unique energy distribution and therefore is best suited to a particular need. In alternative embodiments, as shown in FIGS. 5A-5F, fiber tip 47 may be shaped in a plane normal to the longitudinal axis 43 (see FIG. 5A) or, a concave shape (see FIG. 5B) or a convex shape (see FIG. 5C) to obtain virtually any desirable spot size on the target tissues. In addition to controlling laser spot size, it may be desirable to control the direction of the laser energy being delivered from distal tip 47. As shown in FIG. 5D, distal fiber tip 47 may have a beveled face to form a cone shaped pattern of light pointing downward from the face. As shown in FIG. 5E, a beveled faced distal fiber tip 47 may further include a microprism 40 that provides directional control of the light pattern. As shown in FIGS. 20A-B, a cone-shaped laser energy distribution is delivered from the beveled faced fiber tip 47 such that fiber tip 47 may be oriented for precise photoablation of the target tissues. If desired, the inclined shape of distal end of probe 23 may be aligned with beveled face fiber tip 47. Fiber tip 47 may extend beyond distal end 41 to enable more precise control over the procedure.

Figure 5F:
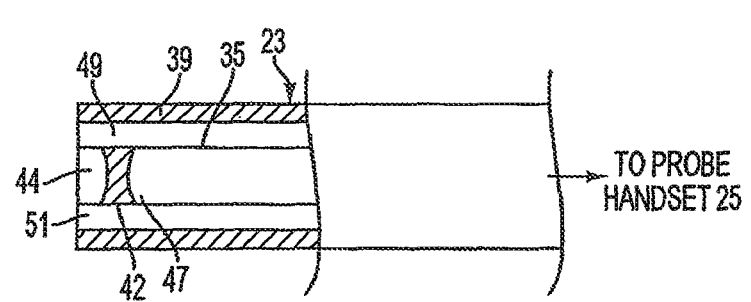

Other mechanisms may be used to control the laser spot size. As shown in FIG. 5F, a transparent spacer or window 44 may be abutted by a micro lens 42 (or a microprism) and is attached to distal fiber tip 47 to achieve a desired spot size of the laser energy on the target tissues. Micro lens 42 is designed such that the target area or spot size, energy distribution and direction of the laser energy can be controlled. Spacer 44 prevents fiber tip 47 from contacting target tissues during the photoablation process. Such arrangement reduces any likelihood that waste products from the process are deposited on the fiber tip 47. Fiber tip 47 may also be maintained free of waste material collecting on it by providing a gas or fluid flow, including a viscoelastic fluid, across the tip. It should be recognized that micro lens 42 and the spacer are generally sized so as to match the diameter of the attached optical fiber.

Figure 19:
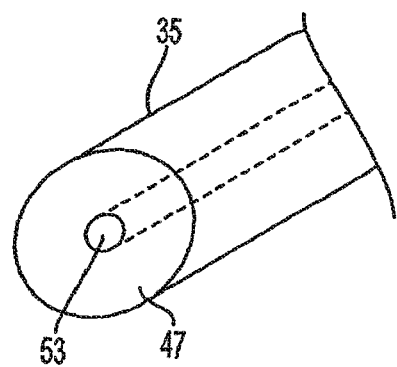
FIG. 19 is a schematic diagram of an irrigation system for use a laser delivery system.

Still referring to FIG. 4, in order to reduce or control possible damaging thermal effects on the target tissues, an irrigation fluid, such as a saline solution, is provided to cool the target tissues. The irrigation fluid is generally aspirated from the eye to prevent overpressure and vent gases during photoablation. Fiber-optic probe 23 may include side-by-side semicircular passageways within and along the interior of sleeve 39 forming an irrigation flow path 49 and a separate aspiration flow path 51. Distal end 41 of probe 23 includes terminal openings for flow paths 49, 51 at distal end 41. These openings may also be positioned along the probe near the terminal end. The terminal openings may be coaxial or in an angled relationship to the light transmitting core 33. Proximal end 45 of probe 23 links flow paths 49, 51 into corresponding flow paths in handset 25. The coupling can be accomplished by known approaches for laser probes. Although the irrigation and aspiration flow paths 49, 51 have been described been in a side-by-side relationship within the sleeve 39 they may also be provided as concentric tubes about a central optical fiber or the infusion/aspiration path flow may be central and the optical fiber adjacent its periphery. Referring to FIG. 19, it is contemplated that fiber optic core 33 may have a hollow cylindrical pathway 53 extending along the center axis for providing irrigation or an aspiration pathway as desired. In addition, alternative approaches of the flow path construction based on fiber optics advances may be employed with optical fibers up to 100 microns. Also, other specialized fibers can enable the associated irrigation and aspiration passageways to be arranged in other ways including within the fiber core(s).

Continuing to refer to FIG. 4, flow paths 49, 51 in probe 23 are connected to an irrigation system 55 and an aspiration system 57 of laser delivery system 21. Each system 55, 57 will be described in detailed herein. Irrigation system 55 supplies a desired irrigation fluid into probe handset 25 via a flexible tubular line under a gravity-feed configuration or a pumped configuration. In the case of a pump configuration, the irrigation fluid is pumped from a sterile reservoir or container 24 into handset 25; the fluid then flows under pump pressure in irrigation pathway 49 to probe 23 distal end 41 and to target tissues.

Figure 1:
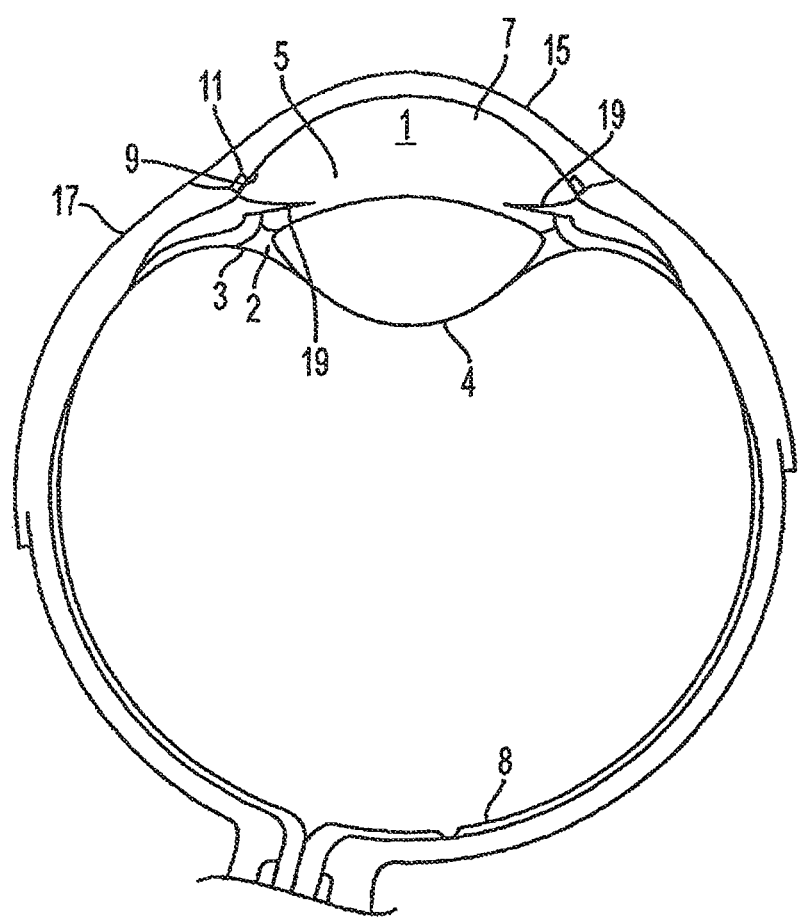
FIG. 1 is schematic sectional view of an eye illustrating the interior anatomical structure.
Figure 2:
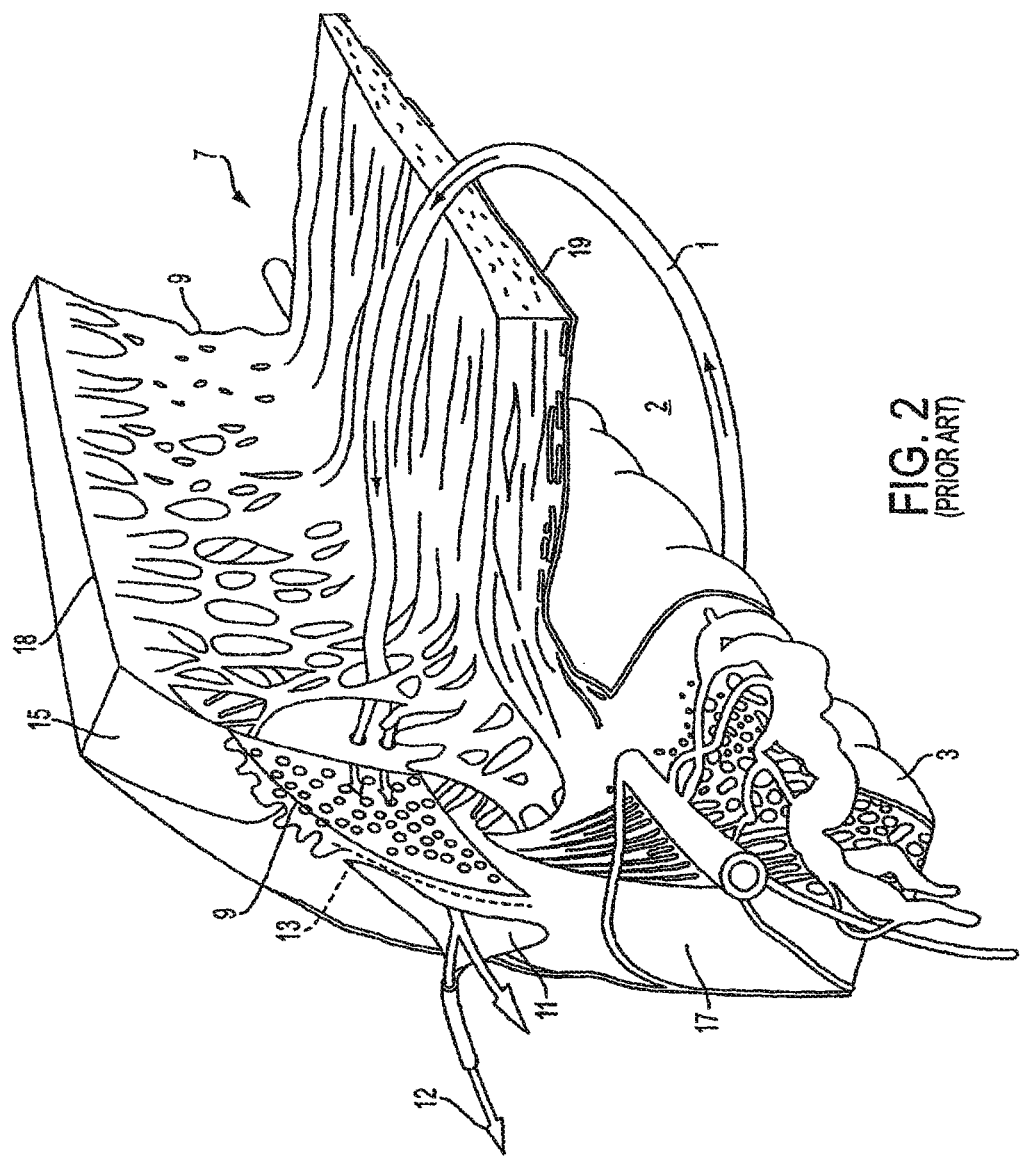
FIG. 2 is a perspective fragmentary view of the anatomy within the anterior chamber of an eye depicting the corneoscleral angle.

Rather than using an irrigation fluid for cooling the target site, a viscoelastic fluid from the irrigation system 55 can be pumped into handset 25 and into probe 23 for cooling the target site. In addition, a viscoelastic fluid may also be used to compress or flatten the trabecular meshwork in the eye, to control its dimensions. Viscoelastic materials for use with the present invention ideally should have a molecular size that is larger than the pore size of the target tissues in order to be able to tampanade or push away the tissue rather than diffusing into it. Properly selected viscoelastic fluids can be used to compress the trabecular meshwork 9 (see FIG. 2) to a reduced thickness and to stabilize the meshwork for eventual removal of selected portions of tissue by laser photoablation.

Alternatively, a viscoelastic fluid may include combinations of therapeutic agents to prevent inflammation at the target site for keeping the apertures open. For example, viscoelastic fluid may be combined physically and/or chemically with, anti-inflammatory agents, steroidal and non-steroidal, anti-angiogenic agents, anti-fibroblast agents, and various other combinations of agents. Specific examples of these types of agents include DFU, which is a nonsteroidal anti-inflammatory, anecortave acetate which is one of the angiostatic steroids, and anti-TGF which is a monoclonal antibody known to inhibit the activity of all three forms of TGF-.beta. in vivo. An example of an available viscoelastic material having a non-steroidal anti-inflammatory agent is disclosed in U.S. Pat. No. 5,811,453 to Yanni et al., which is herein fully incorporated by reference.

Figure 6:
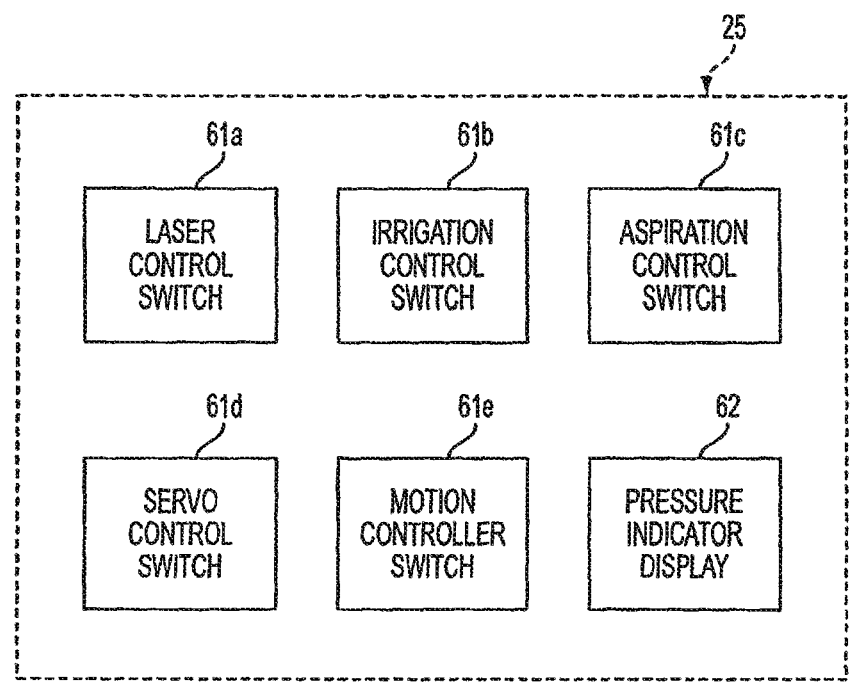
FIG. 6 is a schematic diagram of an embodiment of control switches as may be on a handset for a fiber-optic probe.

Controls switches 61 on the handset 25, a foot pedal, or other control device may be used by the surgeon to initiate flow of the fluid by valve and/or pump control. Irrigation fluid flow may be commenced along with the laser energy delivery to the target tissues. Alternatively, the flow of fluid with the start of laser unit 31 may be automatically regulated by other devices. Referring to FIG. 6, handset 25 may include a plurality of control switches 61a-61e for operating laser delivery system 21.

Control switches 61a-61e perform the same or all of the following functions for operating laser delivery system 21, such as switch 61a for arming and firing laser unit 31; switch 61b for controlling irrigation system 55; switch 61c for controlling aspiration system 57; switch 61d for controlling servo device 27, and switch 61e for controlling motion controller 29. The control switches optionally may be mounted on a separate unit, such as a remote control unit.

Aspiration system 57 enables the extraction of fluid from the eye and also enables immediate extraction of the gases generated from the photoablative decomposition process to escape through aspiration flow path 51 through flexible lines in handset 25. Aspiration system 57 may function passively or may include a sufficiently sized vacuum pump for enabling waste fluid to be suctioned into a waste container or canister 58. Aspiration system 57 allows gases to be removed without otherwise heating the local tissues. Thus, aspiration system 57 advantageously reduces thermal tissue damage.

Laser delivery system 21 may further include a laser unit 31 for providing a beam of periodic light pulses of sufficient fluence to initiate and sustain photoablation of the target tissues in contact with distal end 47 of probe 23. In one embodiment, laser unit 31 comprises a xenon chloride excimer laser operating at a 308 nm wavelength having a fluence ranging from 1 to 60 mJ/mm .sup.2 per pulse and a repetition rate ranging from 5 to 75 Hertz. The corresponding repetition rate can be varied to compensate for the thermal time constant of the tissues in relation to the fluence of the laser energy radiating the target tissues. The 308 mm wavelength is selected to be absorbed preferentially by eye tissues rather than any intervening aqueous humor or any viscoelastic fluid between the tissues. The previously described laser parameters significantly reduce the thermal component of the laser energy and accordingly, resultant collateral tissue damage is minimized. Alternatively, laser unit 31 may be a solid state 2.94 micron Er:YAG laser. This wavelength may be delivered to the target tissue through probe 23 via light transmitting core 33. In addition, laser unit 31 may includes a safety circuit to preclude inadvertent triggering. The various laser parameters may be adjusted accordingly to calibrate laser unit 31 for use on a variety of target tissues. A 355 nm solid state laser may also be used as laser unit 31. One of ordinary skill in art may consider calibration factors such as the homogeneity of the output of the light beam, minimizing the pulse-to-pulse energy variation, the suprathreshold fluence value, and reducing the thermal component of laser-tissue interaction.

In an alternative embodiment, a laser operating at wavelengths in the ultraviolet range from 100 to 400 microns may be utilized to cause photoablation of the target tissues. In yet another embodiment, a laser operating in the infrared wavelengths ranging from 2.5 to 6.5 microns may also comprise laser unit 31. In seeking to minimize the thermal damage to target tissues, if the temperature in the target site reaches a predetermined level established as undesired, then the periodic time between pulses may be lengthened in the range from 5 to 20 Hz. Generally, for use with the present invention, the lasers selected have a short penetration depth which allows for sufficient precision per laser pulse and controlled energy distribution. With ultraviolet lasers, the penetration depth is typically in a range from 0.5 to 1.5 microns; for infrared lasers, the penetration depth is typically in a range from 1-2 microns.

Figure 7:
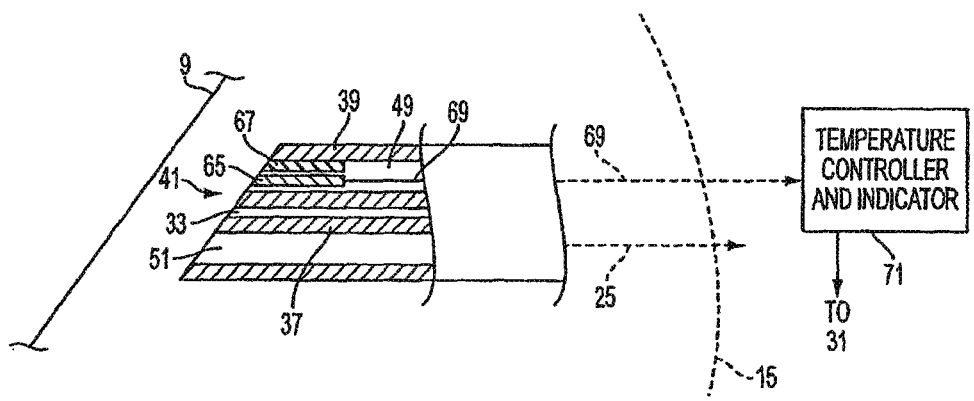
FIG. 7 a schematic diagram of an embodiment of temperature sensing circuitry of a laser delivery system.

In one embodiment, as illustrated in FIG. 7, laser delivery system 21 may include temperature measurement circuitry for sensing temperature at and around the target site and for minimizing collateral thermal damage at and around the target tissues. In this embodiment, distal end 41 of probe 23 may include a thermocouple 65 that is thermally isolated from sleeve 39 by an insulating pad 67. Thermocouple 65 and insulating pad 67 are sized for use with probe 23. Conductors 69 from the thermocouple 65 extend through probe 23 to transmit a feedback signal to an external controller 71. The external controller 71 may indicate or otherwise display the internal temperature sensed by thermocouple 65. In one arrangement, controller 71 alerts the surgeon when the temperature exceeds a predetermined level. If desired, external controller 71 may be operatively coupled to laser unit 31 for automatically self adjusting the repetition rate of the laser based on the sensed temperature. This enables external controller 71 to operate to minimize the thermal effect on the target tissues. Probe sleeve (stainless steel) may be cooled externally near the handpiece cooling flow may be conducted along the sleeve to affect the probe tip and adjacent tissues.

Figure 21A:
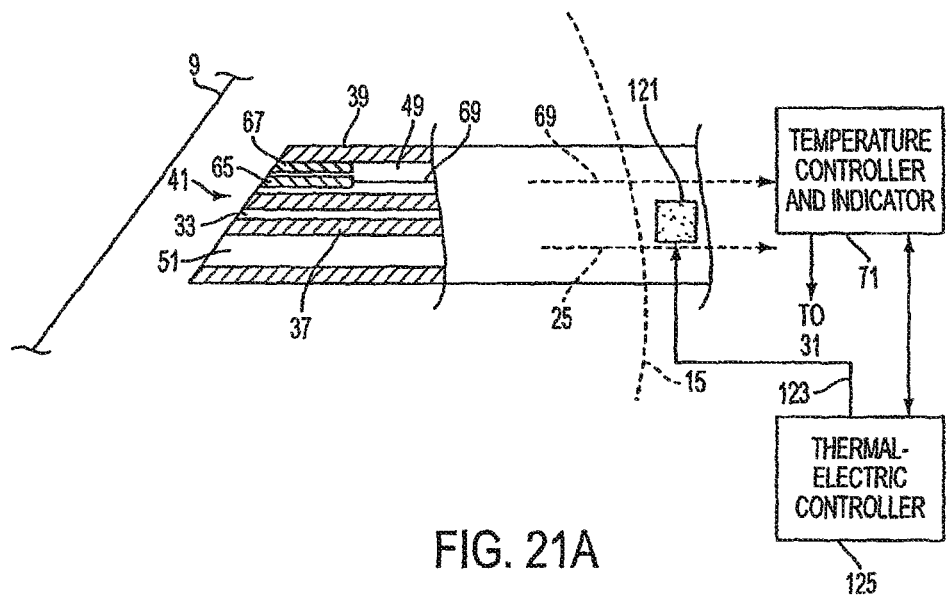
FIGS. 21A-21B are schematic diagrams of alternative heat extraction systems for a probe in accordance with the present invention.
Figure 21B:
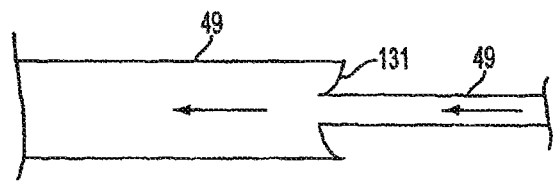

Fiber optic probe 23 may also include a heat extraction system for reducing the thermal component of the laser-tissue interaction during the photoablation period. By removing heat, the heat extraction system may be used to complement the minimal thermal tissue removal of laser unit 31 in order to reduce collateral damage to target tissues from the laser energy. The heat exchanging system may cool sleeve 39 of probe 23 by a heat sink. In one arrangement, the heat sink may be a cooling working liquid that flows in the interior of probe sleeve or cools the probe sleeve by conduction from the handpiece. As shown in FIG. 21A, in an alternative arrangement, an appropriately designed thermoelectric device 121 may be mounted in the interior of the probe 23 or the handpiece 25, such a Peltier cooling device for example. Thermal electric device 121 may be sealed from the fluid in aspiration pathway 51. Device 121 may be coupled to tubular sleeve 39 such that heat may be removed from the surrounding fluid in the eye contacting probe 23. In this case, device 121 may be fluid or water cooled such that fluids flowing in aspiration pathway 51 transfers heat from device 121 to waste container 58. Alternatively, thermal electric device 121 may be mounted on the exterior of tubular sleeve 39 near proximal end 45 in handset 25. In such a case, device 121 may be air cooled for transferring extracted heat to the air. In both cases, signal wire 123 provides electric power to operate device 121 and extends to a thermal electric controller 125. Controller 125 controls the operation of device 121 by turning electric power on and off. Controller 125 may be coupled to external controller 71 in order to operate thermal electric device 121 when the sensed temperature in the eye reaches a predetermined level. A thermal insulating sleeve may be provided on the exterior of tubular sleeve 39 to prevent cooling of the cornea and/or the anterior chamber by probe 23. The thermal insulating sleeve may extend near the proximal end of probe 23. Other cooling alternatives may include Venturi cooling or convection cooling. Referring to FIG. 21B, with Venturi cooling, a Venturi orifice 131 may be mounted in irrigation pathway 49. One skilled in the art would recognize various other alternatives to cooling the probe may be performed.

Figure 8A:
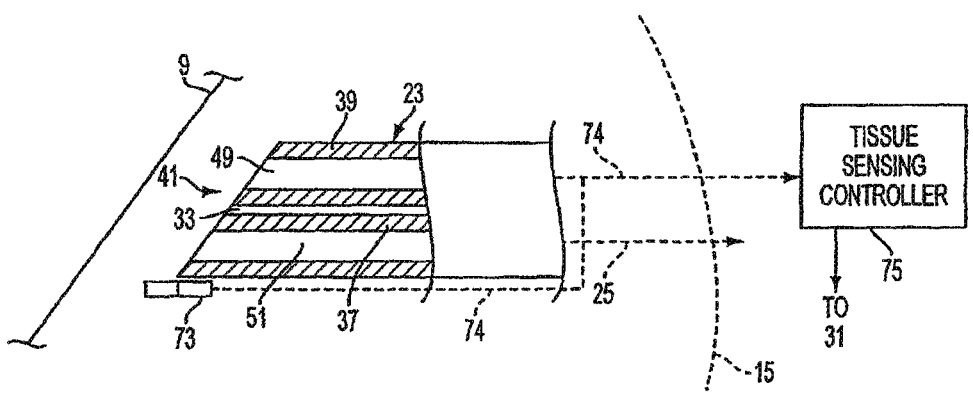
FIGS. 8A and 8B are schematic diagrams of various tissue sensing circuitry for use in a laser delivery system.

In another embodiment, referring to FIG. 8A, laser delivery system 21 may include tissue sensing circuitry for determining when fiber-optic probe 23 is adjacent to or in contact with tissues in the target site. In one arrangement, distal end 41 of probe 23 includes a microswitch 73 for sensing physical contact with tissues, for example, the trabecular meshwork 9. Microswitch 73 may be constructed from a biocompatible material suitable for internal use. Microswitch 73 may be formed in a number of configurations as long as a contact signal is transmitted via signal wires 74 to controller device 75. Signal wires 74 may be installed in a small liquid-fight conduit inside of probe 23 that extend to the proximal end. The contact signal may be a completion of an electrical circuit between switch 73 and controller device 75. Controller device 75 processes the contact signal which may be used both to alert the surgeon that probe-tissue contact has been achieved and in a feedback loop to control laser functions. The alert may be in the form of a lighted display, sound, or other indicator. In addition, the tissue-contact signal may be processed to prevent triggering of laser unit 31 until tissue contact is achieved. As a result, undesired firing of laser unit 31 is avoided, thus reducing the chance of overheating the aqueous humor or other fluid in the anterior chamber. It should be recognized that the tissue-contact signal ceases when microswitch 73 is deactivated by not being in contact with the tissue.

Figure 8B:
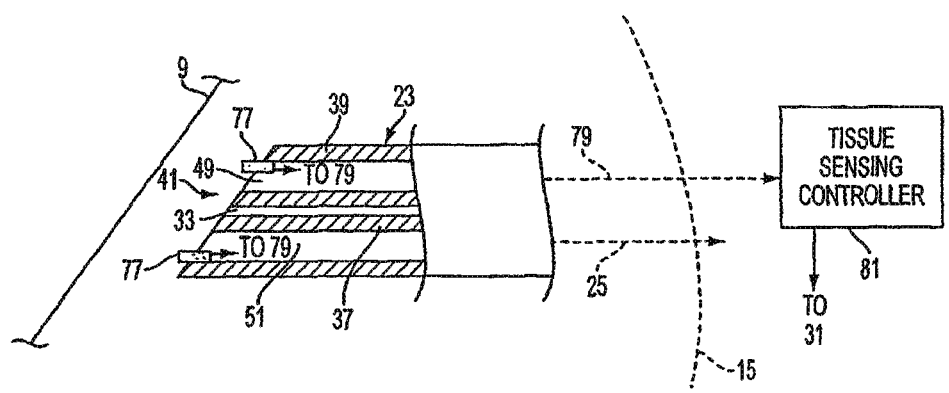

Turning to FIG. 8B, contact with the eye tissue, such as the trabecular meshwork, alternatively may be detected by a pair of microelectrodes 77 mounted on an insulator substrate at distal end 41 of probe 23. Microelectrodes 77 are coupled to signal lines 79 that extend along sleeve 39 to an external gap detector circuit 81. The circuit 81 responds to a threshold change in conductivity or capacitance when the target tissues, for example, the trabecular meshwork, are contacted or within an adequately small distance from the tip. Distance is defined as a function of the dielectric using the probe as one plate and the tissue as a second plate of a capacitor. In order to detect a change in conductivity or capacitance, it is recognized that the aqueous humor and the trabecular meshwork possess different dielectric values. Referring to FIGS. 3 and 8B, when probe 23 enters the anterior chamber 7, the electrodes 77 are located in the aqueous humor. When microelectrodes 77 enter or contact the trabecular meshwork, for example, the dielectric value between the electrode changes. As a result, there is corresponding change in capacitance indicating that probe 23 has contacted tissue.

Laser delivery system 21 may include circuits for preventing the firing of laser unit 31 when the fiber tip 47 is too far separated from the target tissue in order to prevent undesirable thermal heating of aqueous humor and/or the viscoelastic fluid. This is achieved by the probe-tissue contact signal generated by microswitch 73 (FIG. 8A) located at distal end 41 of probe 23. The probe-tissue contact signal is triggered by conductivity changes occurring to tissue compression and relative tissue/aqueous composition. Alternatively, probe-tissue contact signal or a proximity signal, as previously described, may be generated by microelectrodes 77 (FIG. 8B) located at distal end 41 of probe 23 to prevent firing of laser unit 31. Also, the handset 25 may use the signal to activate the laser unit 31 or allow it to be fired if further closure of the gap is needed.

Figure 9:
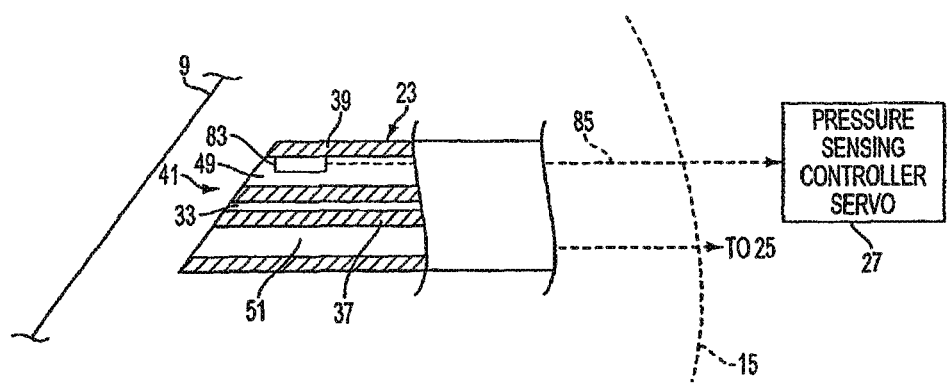
FIG. 9 is a schematic diagram of pressure sensing circuitry of a laser delivery system.

Turning to FIG. 9, laser delivery system 21 may include pressure sensing circuitry for detecting and controlling pressure both at the surgical site and within the anterior chamber during an ophthalmic procedure. Distal end 41 of sleeve 39 may include a pressure sensing transducer 83 for transmitting a feedback pressure signal via signal wires 85 to servo device 27 in order to control the pressure so that target tissue manipulation may be controlled. Signal wires 85 extend from the distal end to the proximal end of probe 23 for operatively coupling to handset 25 and servo device 27. Similar to the tissue sensing circuitry embodiment, signal wires 85 may also be in a liquid-tight conduit located inside of the probe. It should be recognized that the pressure sensing transducer might also be located near the probe tip or in the irrigation pathway and in addition, may be located proximal to the tip along the probe within the anterior chamber.

Figure 10:
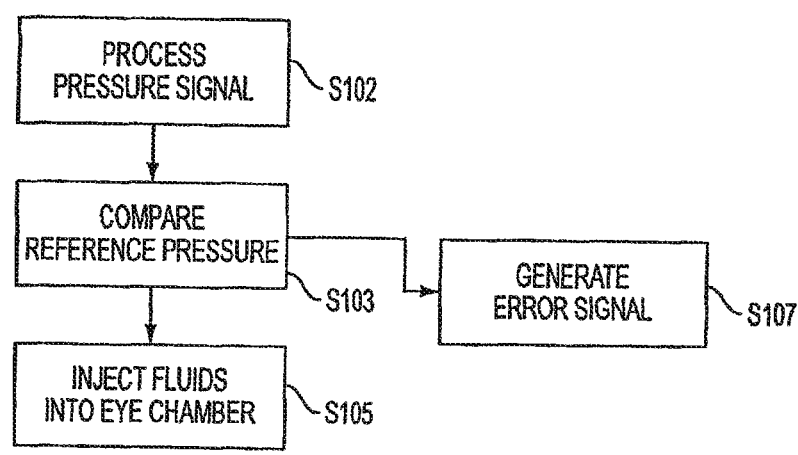
FIG. 10 is a flow chart of an embodiment of operating a servo device of a laser delivery system.

Referring to FIGS. 4 and 10, servo device 27 may include a microprocessor circuit having associated operating software for reading the pressure signals and translating the signals into machine readable code. This may be accomplished with appropriate analog to digital converter devices, as is known in the art. Servo device 27 continuously monitors and regulates the pressure during an ophthalmic procedure, in particular a method of treating glaucoma. Referring to FIG. 10, in order to regulate pressure, in step S101, servo device processes pressure signals from pressure sensors 83. In step S103, the pressure signals are compared with a desired reference pressures. In step, S105 servo device 27 injects fluids, such as a viscoelastic fluid, into anterior chamber 7 of the eye in order to maintain the reference pressure or to adjust to a desired pressure level. In addition, in step, S107, servo device 27 may generate an error signal when the sensed pressure level becomes other than the desired reference level. Optionally, a pressure indicator display 62 may be located on handset 25. Pressure sensor 83 may be located at a distal end of probe 23. In addition, pressure sensor 83 may be located along the shaft of probe 23. Optionally, more than one pressure sensor may be mounted on probe 23 at various locations.

Figure 11A:
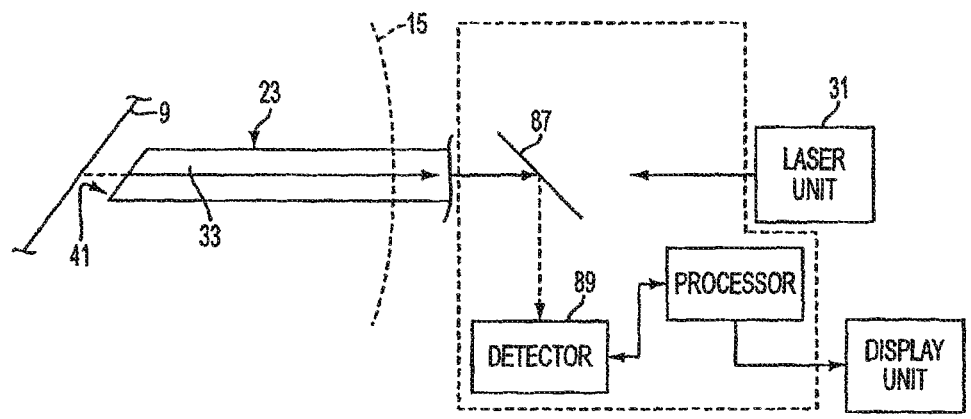
FIGS. 11A-B are schematic diagrams of alternative embodiments of tissue guidance circuitry of a laser delivery system.

Laser delivery system 21 may also include tissue recognition guidance circuitry for detecting penetration into Schlemm's canal by advancement of fiber-optic probe 23 or by laser energy. The tissue recognition guidance circuitry provides information regarding where the probe is located relative to target tissues. In one arrangement, as illustrated in FIG. 11A, a form of optical spectroscopy is employed in which laser light pulses reflected from the target tissues create a back-scattered signal. Optical spectroscopy measures the interaction of light within tissues and provides information for diagnosis at the structural and pathophysiological level with intact tissues, as is known in the art. The back-scattered signal may be deflected off a dichroic mirror 87 in-line with an optical fiber 33 which may be the same fiber used to transmit the laser light or a separate detection fiber to an appropriate detector 89. This enables precise identification of the spatial movement of the fluid, for example, from the anterior chamber to the interior of Schlemm's canal. Alternatively, as part of the optical spectroscopy, a separate optical fiber for returning the back-scattered signal to the detector may be employed. In either case, as is known in optical spectroscopy, the back-scattered signal provides information concerning the relative positions of the probe and the target tissues. Photoacoustic spectroscopy may be used in place of optical spectroscopy. In photoacoustic spectroscopy, incident light is modulated to generate acoustic frequencies. In either case, light signals may be reflected off the target tissue generating a signal reflecting the relative position of the probe to the target tissues. It should be noted that it may be possible to determine the location of the probe relative to target tissues by direct visualization though the primary and or accessory optical fibers.

Figure 11B:
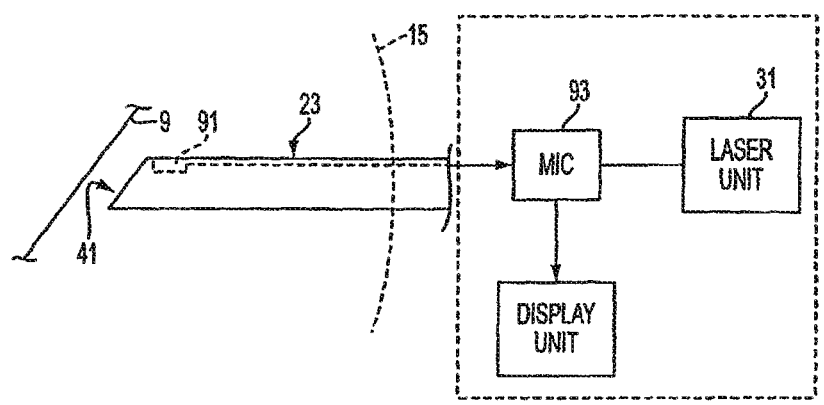

In another arrangement, as illustrated in FIG. 11B, a form of photoacoustic spectroscopy, which allows tissue imaging and depth profiling as is known in the art, implements an acoustic pulser 91 for transmitting signals along the probe 23 to a sensitive capacitive microphone 93 in order to sense the generated pressure fluctuations. The generated echo would be in a frequency range less than 50 KHz. The principles of photoacoustic spectroscopy are well known in ophthalmology.

Figure 12:
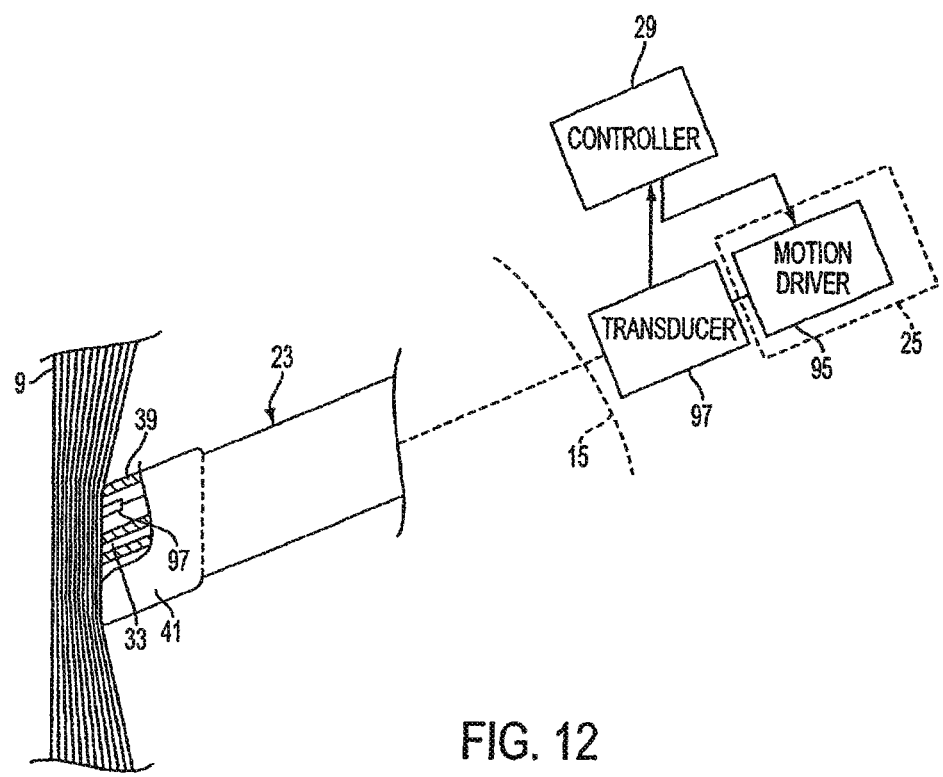
FIG. 12 is a schematic diagram of an embodiment of a motion controller for a fiber-optic probe.

Referring to FIG. 12, laser delivery system 21 may further include motion controller 29 for enabling a controlled rectilinear movement of probe 23 into and through a target tissue site, such as the trabecular meshwork. This is achieved by blunting a portion of distal end 41 of probe 23 to enable sufficient contact against target tissues, such as the trabecular meshwork, with a controlled force produced by a mechanical or hydraulic apparatus. Motion controller 29 includes a limited motion driver 95, such as one using a sensitive miniature voice coil, employed in handset 25 to move the blunt end of probe 23 against the tissues, such as the trabecular meshwork, at a controlled rate and through a precise distance. A force transducer system 97 senses the axial force applied to the tissues when a reactive resistance force is increased. The motion controller 29 slows probe movement when the tissues are compressed to a desired thickness. This type of automatic system provides precise controlled movement and operates more steadily than a manually operated probe. One skilled in the art would recognize various hydraulic or mechanical and controllable systems may be used for the purpose of moving probe 23 in a controlled movement. Motion controller 29 thus proves for controlled movement with micron precision. As illustrated in FIG. 12, precise controlled movement as provided with an automatic system is useful for compressing the trabecular meshwork 9.

Distal end of fiber-optic probe 23 may include a device for viewing probe contact with target tissues. Such a device may have an optical fiber particularly used for viewing the target site, similar to that used in an endoscope that facilitates the viewing. A non-coaxial endoscope may also be used. Positioning can be detected by direct view, or by increasing the intensity of backscattered light or by interferometry.

FIG. 13 illustrates a method of facilitating the drainage of aqueous humor by creating a flow pathway via or circumventing the trabecular meshwork and juxtacanalicular trabecular meshwork, into Schlemm's canal of an eye in order to reduce intraocular pressure. Generally, a distribution of spaced apart radial passages in the periphery of the eye is established to assure relief of intraocular pressure. In step 201 of FIG. 13, the anatomic relationships of the target and adjacent tissues are analyzed. More specifically, anatomic landmarks are identified and relationships between those landmarks are noted. Available equipment employing ultrasonic spectroscopy and optical coherent tomography may be utilized for anatomic tissue localization both prior to and during the method. Once the anatomic factors are determined, the surgeon can visualize and study the position of the visible trabecular meshwork through a goniolens 97 and a typical operating microscope used in ophthalmic surgery. The surgeon is ready to continue with the procedure once landmarks are identified, including Schwalbe's line, the scleral spur and possibly Schlemm's canal.

Referring to FIGS. 3 and 13, in step 203, a small self-sealing incision or paracentesis opening 14 is made in the cornea 15 or sclera 17 to allow access to the target site. The small size of the initial opening in the cornea or the sclera introduces a minimal entry trauma, and the small size facilitates self-closure without suturing in most instances. In step 205, the anterior chamber is stabilized with viscoelastic and fiber optic probe 23 is advanced into the opening 14 and into anterior chamber 7. At step 207, probe 23 is advanced through the anterior chamber according to transocular movement to position distal end 41 of probe 23 in contact with or adjacent to trabecular meshwork 9. A determination of whether probe 23 should be in contact with or adjacent to trabecular meshwork 9 depends on the physical characteristics of the particular site and is made by the surgeon and is within ordinary skill in the art. For the purpose of the present invention, the probe 23 should be within an operable limit of the trabecular meshwork, that is, it should be in contact with or adjacent to the trabecular meshwork in order to enable photoablation at the target tissues, as determined by one of skill in the art.

In step 209, a desired target area is identified so as to position distal end 41 of probe 23 in a direction relative to Schlemm's canal 11 in order to penetrate its inner wall adjacent to the anterior chamber. Positioning distal end 41 of probe 23 will depend on the energy distribution of the selected probe tip 47. As previously described, numerous probe tip designs may be used, depending on need. Several techniques may be used to identify the desired target tissues. In one technique, if Schwalbe's line 18 (FIG. 8) is visible, then a measurable reference exists that may be used to relate to the length of sleeve 24 at its distal end. More specifically, probe 23 may be positioned at the identified anatomic landmark, such as Schwalbe's line 28. Alternatively, a radial indicator, such as a spur or other marker/spacer, extending radially from sleeve 39 distal end 41 but designed to enter at the opening 14 may also be employed. Yet another alternative, includes utilizing a coaxial endoscope located near the distal tip for viewing the trabecular meshwork 9 and resultant positioning distal end 41 of probe 23. An endoscope may also be used through a separate self-sealing incision. In another alternative, an ultrasound detector or scanner may provide a graphical representation of the tissue anatomy and position of distal end 41 of probe 23 to allow locating the distal end with precision relative to Schlemm's canal, as in Ascan ultrasonograph or ultrasonic biomicroscopy. Ultrasonic biomicroscopy is the technology in which high frequency ultrasound (40-100 MHz) is used to produce images of biological structures with resolution approaching 20 micrometers. The structures of interest must be located within 4 mm of the surface of the body or be accessible by an endoscope because of increased loss of ultrasound at high frequencies. Regardless of technique used, a landmark, such as Schwalbe's line, is identified. Next, the energy distribution of a selected probe tip 47 is identified. The probe 23 is then applied to the identified landmark so that photoablative energy may be applied from probe tip 47 in a manner applicable to the target tissues.

At step 211, the intraocular pressure may also be monitored by pressure sensor 83 at distal end 41 or at an intraocular portion of the probe 23. Alternatively, an external pressure sensor or transducer may be used to monitor the internal pressure in the stabilized anterior chamber within desired limits. At step 213, the control switches may be operated by the surgeon to arm the laser for firing into the target site.

Optionally, as shown in step 215, the trabecular meshwork 9 may be compressed or flattened to a general thickness of about 90 microns to reduce the amount of laser radiation and increase treatment rate. Compression of the meshwork reduces the distance of penetration through the trabecular meshwork from approximately 150 microns to about 90 microns, before the distal end 41 of probe 23 reaches Schlemm's canal. Because each light pulse ablates about 1 or 2 microns of tissue when using a 308 nm excimer laser, the time and number of pulses used for micropenetration is shortened and precision is increased. Compaction also aids in physically stabilizing the meshwork. This compaction causes the number of pulses needed in order to penetrate the meshwork and thus enter Schlemm's canal to range from 10 to 100 pulses for the ultraviolet wavelengths. While in the infrared wavelengths, 1 to 20 pulses typically may be sufficient to penetrate into Schlemm's canal.

With reference to step 215, a number of approaches may be used to compress the trabecular meshwork at the target site. As shown in FIG. 9, one approach includes physically contacting and applying an axial force so that the distal end of probe 23 being blunted pushes against the meshwork Tissue contact sensor 73 may provide appropriate notification of the tissue-contact of probe 23. During the advance of the probe into the meshwork, the surgeon may physically view the compaction of the meshwork using the previously described ultrasound scanner, endoscope, or other viewing systems of the eye anatomy.

In an alternative approach, the viscoelastic fluid of a selected viscosity and molecular size may be used to flatten the trabecular meshwork. Incremental or stepped pressure induced within the eye may be achieved by injecting the viscoelastic fluid from irrigation control 55 by control switches or buttons disposed in handset 25. In the viscoelastic fluid case, the surgeon slowly increases the pressure until the meshwork compresses to a desired thickness. It should be recognized that servo device 27 may also be employed to increase the pressure automatically by feedback of pressure sensor 83 in the manner shown in FIG. 10.

Whether or not the meshwork is compressed, as shown in step 217, laser unit 31 transmits laser energy via fiber optic probe 23 so as to photoablate the juxtacanalicular trabecular meshwork and inner wall of Schlemm's canal in the target site. Optionally, concurrent with activation of the laser (see step 217), the irrigation fluid and/or viscoelastic fluid may be supplied into target site of laser energy application. Also, as shown in step 219, while photoablative laser energy is applied to the target site, irrigation fluid and/or vaporized gases may be aspirated in the region of light energy impingement via the aspiration flow path 51 in fiber optic probe 23. The operation of aspiration control 57 and associated flow path has been previously described.

As an alternative to irrigation fluid, therapeutic agents may be injected into the anterior eye chamber or into Schlemm's canal at or about the same time as photoablation is being carried out to thereby minimize traumatic effects and oppose self-healing tendencies of the eye anatomy. In addition to or separately from anti-inflammatory agents, both steroidal and non-steroidal anti-fibroblastic agents and anti-angiogenic agents, singly or in combination can also be provided. The concurrent application of therapeutic agents advantageously increases the long term benefits of opening the meshwork and Schlemm's canal. It should be recognized that once an opening is created in Schlemm's canal from the fiber-optic probe, the therapeutic agents may be injected into the opening. Specific examples of these types of agents include DFU, which is a nonsteroidal anti-inflammatory, anecortave acetate which is one of the angiostatic steroids, and anti-TGF which is a monoclonal antibody known to inhibit the activity of all three forms of TGF-.beta. in vivo.

Optionally, as shown in step 221, the distal tip 41 of probe 23 may be advanced inwardly during the photoablation of the tissues and, if the meshwork was flattened, there may be relative movement as the meshwork expands around the aperture. Any resultant relative movement may be measured at step 221 and the results of the measurement may provided in a feedback loop to handset 25 to be used to control further movement of the probe 23. A pilot opening may be created into Schlemm's canal. Agents then may be injected into Schlemm's canal causing it to expand such that subsequent openings will be less likely to injure the outer wall. More specifically, in order to protect the outer wall of Schlemm's canal, which should not be punctured, a pilot hole may be created and Schlemm's canal inflated. The pilot hole may be stented, creating a bather. A device known as a trabeculatome may be used as such a barrier. The pilot hole may be created and the and stent inserted from a site internal or external to the eye.

While a skilled surgeon may operate fiber optic probe 23 to penetrate only the proximal inner wall of Schlemm's canal, once in the canal, the distal outer wall should be not penetrated. Creating a passageway into Schlemm's canal should be of a controlled depth, because penetration too great a depth could be more traumatic to a patient, due to contact with or breaching of the distal wall of the canal.

Optionally, as shown in step 223, detection of penetration of the proximal inner wall of Schlemm's canal may be accomplished in a number of approaches. A first approach is optical, i.e., by transillumination; another approach includes viewing an ultrasound scanned image of the target site from an above plan view orientation, e.g., high frequency ultrasound. In a second alternative approach to detect penetration of the proximal inner wall, a chemical or photochemical detection method may be implemented. In this case, for example, a hemoglobin detector is employed to determine that blood flow has been encountered in Schlemm's canal. This may be performed, for example, by optical spectroscopy of oxygenated and deoxygenated hemoglobin, i.e., by using diffused light from red diode absorption (e.g., pulse oxymetry, a common clinical tool). As an alternative to a hemoglobin detection, a sensor, for example, optical spectroscopy detecting fluorescence by illuminating and detecting substances directly or by fluorescent stimulation, may detect the presence of a marker substance (e.g. a fluorescing dye), which may be added to the viscoelastic material injected into Schlemm's canal. Examples of such marker substances include fluorescine, indocyanine green or trypan blue. A third alternative approach is to implement the aforementioned tissue recognition guidance circuitry of laser delivery system 21.

As shown in step 225, once penetration of the proximal wall has been detected, the probe 23 is withdrawn before the distal wall is penetrated. In step 227, probe 23 is repositioned at an accessible new target site for repetition of the sequence. The probe is subsequently moved transocurlary to a number of different angular locations about the corneoscleral angle shown in FIG. 2, in order to create additional radial passages in the periphery of the eye, as previously described. As a result, an adequate number of radial outflow apertures, typically ranging from two to ten, are formed in the juxtacanalicular trabecular meshwork 9 and the proximal inner wall of Schlemm's canal 11. The inner proximal wall of the resultant microsculptured Schlemm's canal will have precisely cut or minimally fused ends of tissue as a result of the process described above. Minimal scarring or shearing of tissue will occur so as to discourage initiation of a significant healing response and to provide for controlling and lowering the intraocular pressure for a longer time as compared with previously used techniques.

Figure 14:
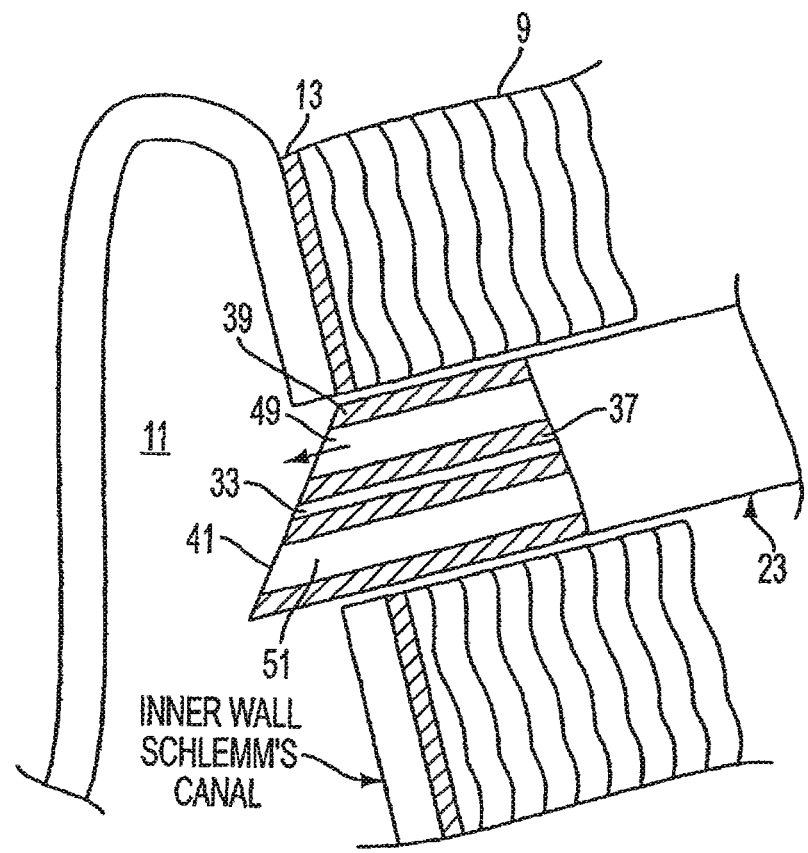
FIG. 14 is a schematic diagram of a fiberoptic probe for providing fluids/materials into Schlemm's canal.

In an alternative embodiment of the method, once Schlemm's canal is penetrated, in step 229, as illustrated in FIG. 14, an appropriate viscoelastic fluid may be injected or coaxially infused so as to inflate or expand the canal. Thereafter, once the probe is repositioned to a new target site, a greater margin of error for photoablation exists to avoid damaging the outer wall. In addition, filling Schlemm's canal with viscoelastic fluid results in a compression of the trabecular meshwork from behind such that, when the meshwork is compressed to lessen the thickness of the trabecular meshwork to be ablated and, in addition, the inner and outer walls of Schlemm's canal stay separated and are prevented from collapsing by the axial compressive force applied by probe 23. In addition, filling Schlemm's canal prevents penetrating the outer wall by providing a larger distance of about 300 microns between the inner and outer walls. It should be recognized that a viscoelastic fluid having therapeutic agents may also be used to expand Schlemm's canal. This use has multiple benefits such as creating a pressure reaction structure, a larger target site to photoablation, preventing penetration of the distal wall of Schlemm's canal, and applying therapeutic agents in all the openings or perforations in a uniform manner. It should be recognized that expansion of Schlemm's canal will usually not have to be repeated once performed. In an alternative, once Schlemm's canal is penetrated, a blocking device such as a tube, stent or viscoelastic material may be placed into Schlemm's canal to prevent injury to its outer wall. This device may also be introduced into Schlemm's canal from outside of the eye via a separate incision.

Figure 15:
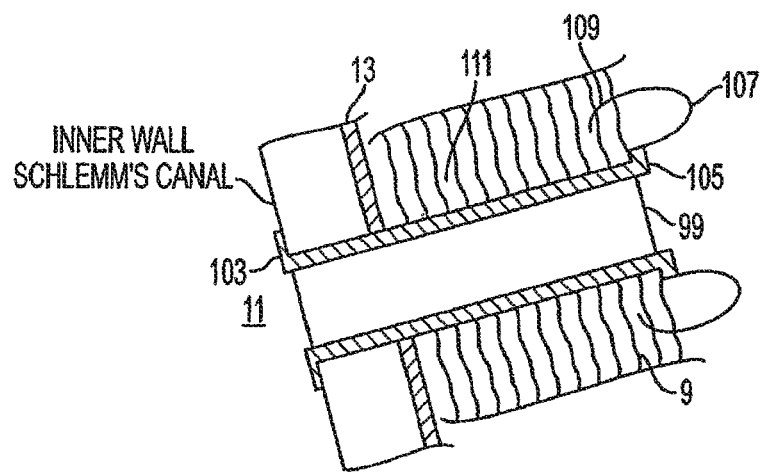
FIG. 15 is a schematic diagram of a first embodiment of an intraocular intracannalicular implant device.

Referring now to FIGS. 15-18B, devices and a technique are shown for controlling the geometry of Schlemm's canal 11 and optionally the trabecular meshwork 9. Referring to FIG. 15, an intraocular implant device 99 is illustrated. Implant device 99 self-retains in the inner wall of Schlemm's canal 11 and may extend into and through the trabecular meshwork 9. Implant device 99 may be embodied in a stent having an elongated tubular body 101. Implant device 99 may include a valve leaflet to ensure unidirectional outflow. The distal end of tubular body 101 may include a plurality of foldable legs 103 for engaging the inner wall of Schlemm's canal when they are fully deployed. The proximal end of tubular body 101 includes a flange portion 105 and a plurality of thin elongated cylindrical projections 107 having hook-like distal ends 109 for linking or hooking into the trabecular meshwork 9.

Figure 16:
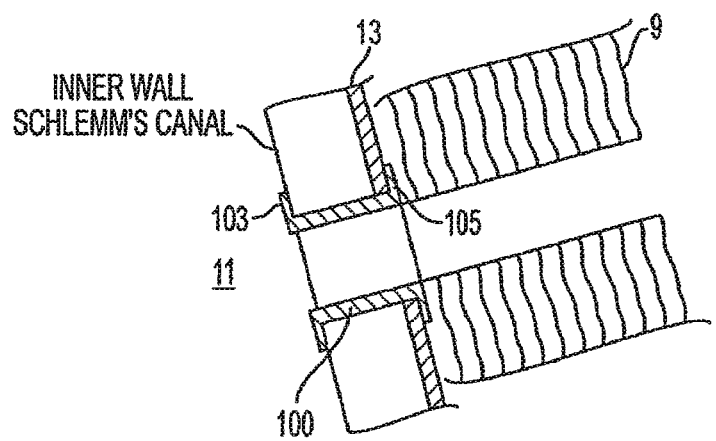
FIG. 16 is a schematic diagram of a second embodiment of an intraocular intracannalicular implant device.

Tubular body 101 may have an inner diameter dimension of 10-200 microns and an outer diameter of less than 1000 microns. Foldable legs 103 typically are in a range from 5 to 50 microns. Cylindrical projections 107 may have dimensions in a range from 5 to 50 microns and appear similar to hooks of Velcro which self-engage and self-retain. Implant device 99 preferably may be constructed from a biocompatible, inert material capable of being sterilized and unlikely to stimulate a foreign body reaction. Tubular body 101 may be constructed from materials such as thermoplastic, stainless steel, PMMA, nylon or polypropylene. Foldable legs 103 and cylindrical projections 107 can be made from one of these same or other materials. With reference to FIG. 16, an alternative implant device 100 is illustrated. Device 100 may be similar to the structure of device 99, except that the tubular body extends only the thickness of the inner wall of Schlemm's canal.

Figure 17:
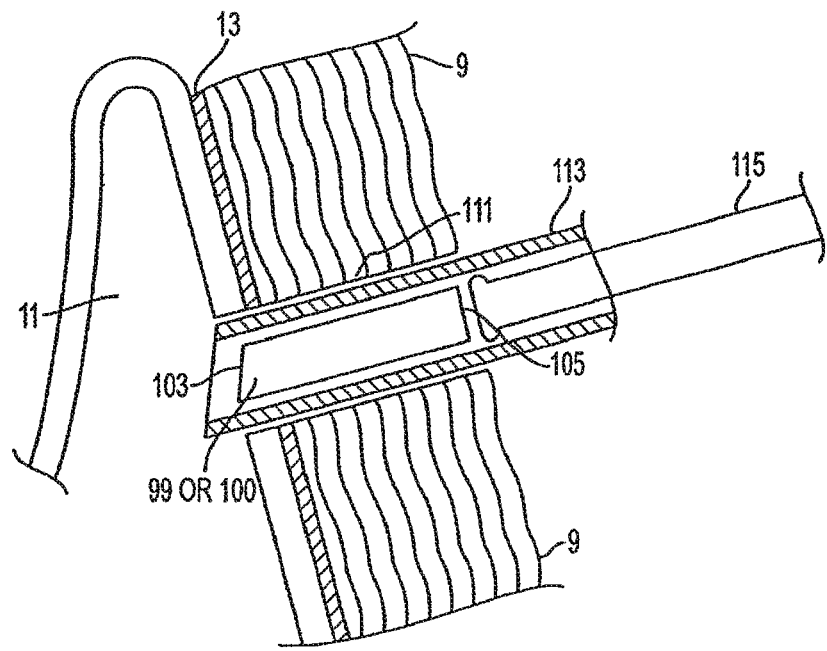
FIG. 17 is a fragmentary schematic diagram of a system for implanting the devices of FIGS. 15 and 16 into the eye.

An embodiment of a system and method of positioning the implant device is illustrated in FIG. 17. A self-sealing opening is created in the cornea of the eye. A cutting cannula or fiber-optic probe 23 may be inserted and advanced transocularly through the anterior chamber to open a cylindrical aperture 111 extending from trabecular meshwork 9 to Schlemm's canal 11. This cannula or the probe may then be withdrawn from the eye. Implant device 99 is retained or carried inside a distal end of an inserter device 113. Such configuration enables the distal end of implant device 99 having foldable legs 103 to be positioned for eventually implantation into aperture 111 and Schlemm's canal 11. The proximal end of implant device 99 abuts a central shaft or plunger member 115. Central shaft 115 is slidably engaged within inserted tube 113. Next, the distal end of inserter tube 113 having implant device 99 is introduced through the opening and advanced to cylindrical aperture 111. Thereafter, the surgeon may position the distal end of inserter tube 113 such that implant device 99 is inserted into the aperture.

Figure 18A:
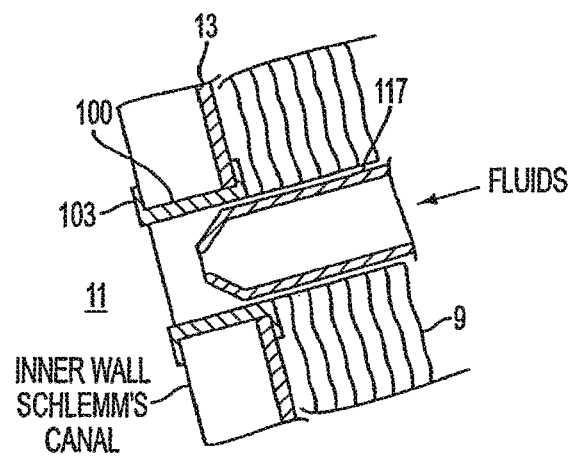
FIGS. 18A-18B are schematic diagrams of a system for providing fluids/materials in Schlemm's canal.
Figure 18B:
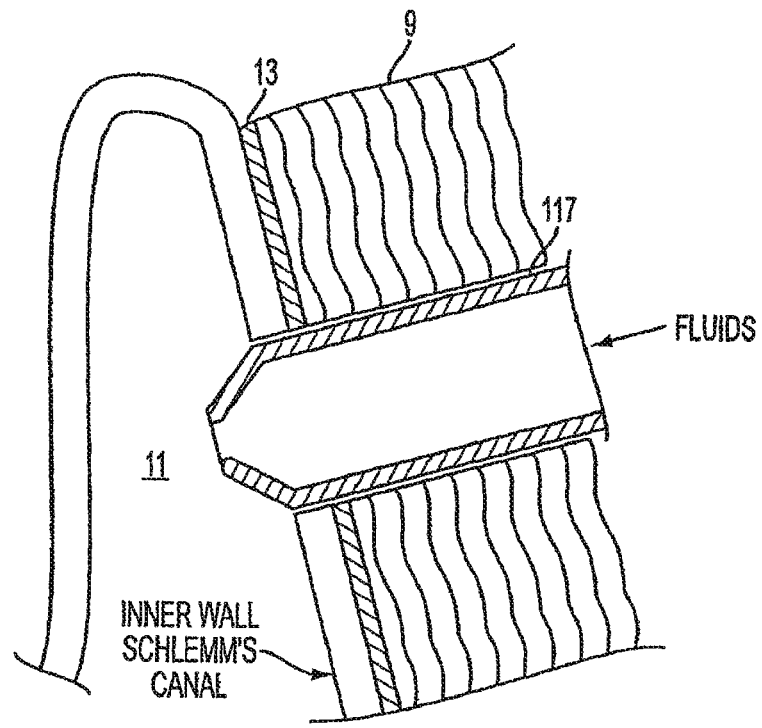

Once the implant device is in the aperture 111, central shaft 115 may be advanced forward to push the distal end of implant device 99 into and through the inner wall of Schlemm's canal 11. Foldable legs 103 are then unrestrained and released into the proximal inner wall of Schlemm's canal 11. The inserter tube and central shaft are withdrawn from the aperture. At this point the cylindrical projections of the proximal end of implant device engage the trabecular meshwork 9. If desired, as shown in FIG. 18A, a feeder tube 117 may abut within the proximal opening of the tubular body and various therapeutic agents or viscoelastic fluids may be provided into the canal. Alternatively, as shown in FIG. 18B, an implant device may be eliminated and feeder tube 117 may be inserted into Schlemm's canal 11 to inject fluids. Nevertheless, it should be recognized that an implant device might be inserted in each aperture created in the trabecular meshwork 9. A grommet unit may be employed instead of a stent, and either may incorporate a one way valve. It should be recognized that inserter device may be configured with circuitry similar to fiber-optic probe 23. For example, distal end of inserted tube 113 may include a tissue-contact sensor to detect when the meshwork is contacted by tube 113.

The system and method of treatment for glaucoma should account for variations in the relative position and character of Schlemm's canal as well as anatomical differences in the trabecular meshwork from patient to patient. It should be recognized that other alternatives may present themselves to those skilled in the art. Fabrication techniques used for miniaturized devices may be employed to form sensors, actuators and conductors on the inserted portion of a probe. The probe may be designed so that it is disposable wholly or in major part. The tip end of the probe may be angled to or deflect off a small mirror or prism according to the angle of the trabecular meshwork. A variety of other types of irrigation and aspiration can be used with the probe to perform the function described. For example irrigation fluid may be fed in between the outside of the metal sleeve and the inner surface of a concentric shield that conforms to and seals the incision or via a separate incision.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. For example, a microdrill may be used employed instead of a fiber optic probe to penetrate the trabecular meshwork and Schlemm's canal. Also it should be recognized that the concept of compressing the eye anatomy with viscoelastic material is applicable to other tissues such as joint cartilage, ligaments, arachnoid tissue and the like and fiberoptically introduced photoablation of these tissues to effect pressure control and tissues removal for alterations of tissue structure, fluid flow and placement of devices such as stents or anchors. The techniques described in the present invention may be used as an adjunct to current endoscopic surgical procedures. More specifically, tissues may be identified endoscopically and photoablated as previously described according to the present invention. Therefore, it is intended that the invention not be limited to the particular embodiment disclosed, but that the invention will include all embodiments falling within the scope of the appended claims.

What is claimed is:

1. A method of treating glaucoma of a patient's eye, the eye comprising an anterior chamber, a trabecular meshwork and a Schlemm's canal, the Schlemm's canal comprising an outer wall and an inner wall, the method comprising:

positioning an intraocular implant to extend through the trabecular meshwork of the eye, the implant having a proximal portion comprising a proximal opening configured to reside in the anterior chamber of the eye, a distal portion comprising a distal opening configured to reside in the Schlemm's canal of the eye, a middle portion comprising a substantially straight passageway extending from the proximal opening to the distal opening, the middle portion dimensioned to extend across the inner wall of the Schlemm's canal and the trabecular meshwork, the distal portion comprising a contact surface to contact an inner wall of the Schlemm's canal, the distal portion sized and shaped to substantially inhibit contact with collector channels on the outer wall of the Schlemm's canal when the contact surface of the distal portion engages the inner wall of the Schlemm's canal and self-retains the implant with engagement of the inner wall of the Schlemm's canal; and wherein fluid is conducted, through the substantially straight passageway, from the opening on the proximal portion of the implant to the opening on the distal portion of the implant, such that fluid flows from the anterior chamber to the Schlemm's canal through the implant.

2. The method of claim 1, wherein the distal portion is sized and shaped to inhibit contact with the collector channels opposite the distal opening when engaging the inner wall of the Schlemm's canal.

3. The method of claim 1, wherein the distal opening is located on a distal end of the distal portion.

4. The method of claim 1, wherein the proximal portion comprises a feature to contact the trabecular meshwork.

5. The method of claim 4, wherein the feature comprises a plurality of projections.

6. The method of claim 4, wherein the feature comprises a flange.

7. The method of claim 6, wherein a distance between a surface of the flange on the proximal portion and the contact surface on the distal portion is sized to allow engagement of the trabecular meshwork with the surface of the flange when the contact surface of the distal portion engages the inner wall of the Schlemm's canal.

8. The method of claim 1, wherein the distal portion comprises a plurality of foldable legs for engaging the inner wall of the Schlemm's canal.

9. The method of claim 1, further comprising providing an inserter device that is configured to carry the intraocular implant and puncture the trabecular meshwork and position the distal portion of the intraocular implant within the Schlemm's canal.

10. The method of claim 1, further comprising inserting the intraocular implant through a corneal incision.

11. The method of claim 1, wherein the outer cross-sectional dimension of the middle portion is less than an outer cross-sectional dimension of the proximal portion.

12. The method of claim 1, wherein the middle portion comprises an outer cross-sectional dimension that is less than a cross-sectional dimension of the distal portion.

13. An intraocular implant for placement in a patient's eye to conduct fluid from the eye to treat glaucoma, the eye having a trabecular meshwork, an anterior chamber and a Schlemm's canal, the Schlemm's canal comprising an outer wall and an inner wall, the implant configured to be positioned such that the implant extends through the trabecular meshwork of the eye, the implant comprising:

a proximal portion comprising a proximal opening configured to reside in the anterior chamber of an eye;

a distal portion comprising a distal opening configured to reside in the Schlemm's canal of the eye;

a middle portion comprising a substantially straight passageway extending from the proximal opening to the distal opening, the middle portion dimensioned to extend across the inner wall of the Schlemm's canal and the trabecular meshwork, the distal portion comprising a contact surface to contact an inner wall of the Schlemm's canal, the distal portion sized and shaped to substantially inhibit contact with collector channels on the outer wall of the Schlemm's canal when the contact surface of the distal portion engages the inner wall of the Schlemm's canal and self-retains the implant with engagement of the inner wall of the Schlemm's canal; and wherein the substantially straight passageway is configured to conduct fluid from the opening on the proximal portion of the implant to the opening on the distal portion of the implant, such that fluid flows from the anterior chamber to the Schlemm's canal through the implant.

14. The intraocular implant of claim 13, wherein the distal portion is sized and shaped to inhibit contact with the collector channels opposite the distal opening when engaging the inner wall of the Schlemm's canal.

15. The intraocular implant of claim 13, wherein the distal opening is located on a distal end of the distal portion.

16. The intraocular implant of claim 13, wherein the proximal portion comprises a feature to contact the trabecular meshwork.

17. The intraocular implant of claim 16, wherein the feature comprises a plurality of projections.

18. The intraocular implant of claim 16, wherein the feature comprises a flange.

19. The intraocular implant of claim 18, wherein a distance between a surface of the flange on the proximal portion and the contact surface on the distal portion is sized to allow engagement of the trabecular meshwork with the surface of the flange when the contact surface of the distal portion engages the inner wall of the Schlemm's canal.

20. The intraocular implant of claim 13, wherein the distal portion comprises a plurality of foldable legs for engaging the inner wall of the Schlemm's canal.

21. The intraocular implant of claim 13, further comprising providing an inserter device that is configured to carry the intraocular implant and position the distal portion of the intraocular implant within the Schlemm's canal.

22. The intraocular implant of claim 13, further comprising inserting the intraocular implant through a corneal incision.

23. The intraocular implant of claim 13, wherein the middle portion comprises an outer cross-sectional dimension that is less than an outer cross-sectional dimension of the proximal portion.

24. The intraocular implant of claim 13, wherein the middle portion comprises an outer cross-sectional dimension that is less than a cross-sectional dimension of the distal portion.

* * * * *